(12) United States Patent
Ben Dror et al.

(10) Patent No.: US 8,470,345 B2
(45) Date of Patent: *Jun. 25, 2013

(54) LIPIDS CONTAINING OMEGA-3 AND OMEGA-6 FATTY ACIDS

(75) Inventors: Gai Ben Dror, Moshav Ofer (IL); Dorit Platt, Shimshit (IL); Orly Farkash, Shimshit (IL); Rassan Zuabi, Afula (IL); Zohar Bar-On, Karmiel (IL); Avidor Shulman, Kiryat Tivon (IL); Dori Pelled, Hod Hasharon (IL)

(73) Assignee: Enzymotec Ltd., Migdal Haemeq (IL)

( * ) Notice: Subject to any disclaimer, the term of this patent is extended or adjusted under 35 U.S.C. 154(b) by 698 days.

This patent is subject to a terminal disclaimer.

(21) Appl. No.: 12/590,893

(22) Filed: Nov. 16, 2009

(65) Prior Publication Data
US 2010/0069332 A1    Mar. 18, 2010

Related U.S. Application Data

(63) Continuation of application No. 11/872,258, filed on Oct. 15, 2007, now abandoned, which is a continuation of application No. 10/994,175, filed on Nov. 19, 2004, now abandoned, which is a continuation of application No. PCT/IL2004/000957, filed on Oct. 21, 2004.

(30) Foreign Application Priority Data

Oct. 22, 2003    (IL) .......................................... 158552

(51) Int. Cl.
*A61K 31/685*  (2006.01)
*A61P 25/00*   (2006.01)

(52) U.S. Cl.
USPC ........................................ 424/400; 514/77

(58) Field of Classification Search
USPC ............................................ 424/400; 514/77
See application file for complete search history.

(56) References Cited

U.S. PATENT DOCUMENTS

| | | | |
|---|---|---|---|
| 5,750,572 A | 5/1998 | Bruzzese |
| 5,925,669 A | 7/1999 | Katz et al. |
| 6,005,004 A | 12/1999 | Katz et al. |
| 6,541,043 B2 | 4/2003 | Lang |

(Continued)

FOREIGN PATENT DOCUMENTS

| | | |
|---|---|---|
| DE | 2907778 | 8/1979 |
| DE | 19943198 | 3/2001 |

(Continued)

OTHER PUBLICATIONS

Tsakiris, S. (1984) Z Naturforsch {C1, 39 (11-12); 1196-8.

(Continued)

*Primary Examiner* — Aradhana Sasan
(74) *Attorney, Agent, or Firm* — John P. White; Cooper & Dunham LLP

(57) ABSTRACT

A lipid preparation including a glycerophospholipid or salt, conjugate and derivatives thereof, particularly phosphatidylserine (PS), phosphatidylcholine (PC), phosphatidylethanolamine (PE), phosphatidyl-inositol (PI), phosphatidylglycerol (PG) and phosphatidic acid (PA), and poly-unsaturated fatty acid (PUFA) acyl groups, particularly long-chain poly-unsaturated fatty acid (LC-PUFA) acyl groups such as omega-3 and/or omega-6 acyl groups, wherein said PUFA is covalently bound to said glycerophospholipid. The preparation possesses an improved bioactivity, and is useful in the treatment of various cognitive and mental conditions and disorders and for maintenance of normal functions of brain-related systems and processes.

10 Claims, 8 Drawing Sheets

U.S. PATENT DOCUMENTS

| | | | |
|---|---|---|---|
| 7,968,112 B2* | 6/2011 | Ben Dror et al. | 424/439 |
| 2005/0130937 A1 | 6/2005 | Ben Dror et al. | |
| 2006/0241080 A1 | 10/2006 | Dror et al. | |
| 2007/0160659 A1 | 7/2007 | Platt et al. | |
| 2008/0085320 A1 | 4/2008 | Dror et al. | |
| 2009/0074857 A1 | 3/2009 | Dror et al. | |
| 2011/0144063 A1* | 6/2011 | Dror et al. | 514/114 |

FOREIGN PATENT DOCUMENTS

| | | |
|---|---|---|
| EP | 0609078 | 1/1994 |
| JP | 03188088 | 8/1991 |
| JP | 06256179 | 9/1994 |
| JP | 06279311 | 10/1994 |
| WO | WO 97/39759 | 10/1997 |
| WO | WO 2004/049907 | 6/2004 |
| WO | WO 2005/038037 | 4/2005 |

OTHER PUBLICATIONS

Kidd, Phophatidylserine: Membrane Nutrient for Memory. A Clinical and Mechanistic Assessment, 1996, Alternative Medicine Review, vol. 1, No. 2, pp. 70-84.
Bligh and Dyer, (1959) Can. J. Biochem. Physiol. 37, 911-917.
Sakai M. (1996) Nutr Sci Vitaminol. (Tokyo) 42(2-1):47-54.
Carrie et al., (2000) J. Lipid Res. 41, 465-472.
Yabuuchi et al. (1968) J. Lipid Res. 9(1):65-7.
Wijendran et al. (2002) Pediatr. Res. 51:265-272.
Lytle et al. (1992) Nutr Cancel.: 17(2):187-94.
Suzuki et al. (2000) Jpn. J. Pharmacol. 84, 86-8.
Drago et al. (1981) Neurobiol Aging. 2(3):209-13.
Voigt et al. (2001) J. Pediatr.; 139(2):189-96.
Zanotti A. et al. (1986) Psychopharmacology (Berl). 90(2): 274-5.
Pearce et al. (1998) Nature 396: 75-77.
Kolanowski et al. (2001) Int. J. Food Sci Nutr.: 52(6):469-76.
Stubberfield et al. (1999) J. Paediatr Child Health; 35:450-3.
Williams et al. (1980) J. Neurochem.; 35, 266-269.
Claro F. et al. (1999) Physiol Behan. 67(4):551-4.
Chalon et al. (1998) J. Nutr.; 128(12):2512-9.
Suzuki et al. (2001) J. Nut. 131:2951-6.
Song et al., Enhanced level of n-3 fatty acid in membrane phospholipids induces lipid peroxidation in rats fed dietary docosahexaenoic acid oil, 2001, Atherosclerosis, 155, pp. 9-18.
O'Brien et al. (1964) J. Lipid Res. 5(3):329-38.
Furushiro M. et al. (1997) Jpn. J. Pharmacol. 75(4): 447-50.
Patent Abstracts of Japan, vol. 018, No. 651 (C-1285), Dec. 9, 1994 & JP 06 256179 (Nippon Oil & Fats Co Ltd), Sep. 13, 1994.
Patent Abstract of Japan, vol. 1995, No. 01, Feb. 28, 1995 & JP 06 279311 (Sagami Chem Res Center; others:01) 4.
Database WPI, Sect. Ch, Week 199139 Derwent Pub Ltd, GB; XP002322994 & JP 03 188088 (Ajinomoto KK) Aug. 16, 1991.
Tochizawa, Kaoru et al: "Effects of phospholipids . . . cells", Nihon Yukagakkaishi, 46(4), 383-90, Coden: NIYUFC; ISSN: 1341-8327, 1997, XP008044295.
Nakashima R et al: "Synthesis of didocasahexaenoylphosphatidylserine", Bioscience Biotech. Biochem., Japan Soc. for Biosci., Biotech. and Agrochem. Tokyo JP, vol. 61, No. 12, 1997, pp. 1991-1994, XP 008044298.
Peter A. Ahmann MD, et al., Placebo-Controlled Evaluation of Ritalin Side Effects, Pediatrics, Jun. 1993, pp. 1101-1106, vol. 91, No. 6.
Semyon I. Aleynik et al., Polyenylphosphatidylcholine Protects Against Alcohol but Not Iron-Induced Oxidative Stress in the Liver, Alcoholism: Clinical and Experimental Research, 2000, pp. 196-206, vol. 24, No. 2.
Marabella A. Alhambra MD, et al., EEG Biofeedback: A New Treatment Option for ADD/ADHD, Journal of Neurotherapy, 1995, pp. 39-43, vol. 1, No. 2.
American Psychiatric Association, Diagnostic and Statistical Manual of Mental Disorders (DSM-IV-TR), 1994, 4th Edition, Washington D.C.
Gwendolyn Barcelo-Coblijn et al., Modification by docosahexaenoic acid of age-induced alterations in gene expression and molecular composition of rat brain phospholipids, PNAS, Sep. 30, 2003, pp. 11321-11326, vol. 100, No. 20, The National Academy of Science of the USA.
Barkley, R.A., Attention-Deficit Hyperactivity Disorder: A Handbook for Diagnosis and Treatment, 1990, Guilford Press, New York.
D. Benton et al., The Influence of Phosphatidylserine Supplementation on Mood and Heart Rate when Faced with an Acute Stressor, Nutritional Neuroscience, 2001, pp. 169-178, vol. 4.
Arjan Blokland, Ph.D. et al., Cognition-Enhancing Properties of Subchronic Phosphatidylserine (PS) Treatment in Middle-Aged Rats: Comparison of Bovine Cortex PS With Egg PS and Soybean PS, Nutrition, 1999, pp. 778-783, vol. 15, Elsevier Science.
Nicole Brossard et al., Human plasma albumin transports [13C]docosahexaenoic acid in two lipid forms to blood cells, Journal of Lipid Research, 1997, pp. 1571-1582, vol. 38.
John R. Burgess et al., Long-chain polyunsaturated fatty acids in children with attention-deficit hyperactivity disorder, Am. J. Clin. Nutri., 2000, pp. 327S-330S, vol. 71.
Irene Colquhoun et al., A lack of Essential Fatty Acids as a Possible Cause of Hyperactivity in Children, Medical Hypotheses, 1981, pp. 673-679, vol. 7.
Julie A. Conquer et al., Fatty Acid Analysis of Blood Plasma of Patients with Alzheimer's Disease, Other Types of Dementia, and Cognitive Impairment, Lipids, 2000, pp. 1305-1312, vol. 35, No. 12.
Marc Enslen et al., Effect of Low Intake of n-3 Fatty Acids During Development on Brain Phospholipid Fatty Acid Composition and Exploratory Behavior in Rats, Lipids, 1991, pp. 203-208, vol. 26, No. 3.
Gordon B. Forbes, Clinical Utility of the Test of Variables of Attention (TOVA) in the Diagnosis of Attention-Deficit/Hyperactivity Disorder, Journal of Clinical Psychology, 1998, pp. 461-476, vol. 54, No. 4, John Wiley & Sons, Inc.
Charles H. Goyette et al., Normative Data on Revised Conners Parent and Teacher Rating Scales, Journal of Abnormal Child Psychology, 1978, pp. 221-236, vol. 6, No. 2.
Pnina Green et al., Modulation of Fetal Rat Brain and Liver Phopholipid Content by Intraamniotic Ethyl Docosahexaenoate Administration, Journal of Neurochemistry, 1995, pp. 2555-2560, vol. 65, No. 6, Lippincott-Raven Publishers, Philadelphia.
Lawrence M. Greenberg et al., Developmental Normative Data on the Test of Variables of Attention (T.O.V.A.), J. Child Psychol. Psychiatry, 1993, pp. 1019-1030, vol. 34, No. 6.
Tomohito Hamazaki et al., Administration of Docosahexaenoic Acid Influences Behavior and Plasma Catecholamine Levels at Times of Psychological Stress, Lipids, 1999, pp. S33-S37, vol. 34, Supplement.
Tony Hayek et al., Increased Plasma and Lipoprotein Lipid Peroxidation in Apo E-Deficient Mice, Biochemical and Biophysical Research Communications, Jun. 30, 1994, pp. 1567-1574, vol. 201, No. 3, Academic Press, Inc.
S. Hirayama et al., Effect of docosahexaenoic acid-containing food administration on symptoms of attention-deficit/hyperactivity disorder—a placebo-controlled double-blind study, European Journal of Clinical Nutrition, 2004, pp. 467-473, vol. 58, Nature Publishing Group.
Barbara V. Howards, Ph.D. et al., Low-Fat Dietary Pattern and Risk of Cardiovascular Disease, JAMA, Feb. 8, 2006, pp. 655-666, vol. 295, No. 6, American Medical Association.
FDA/Center for Food Safety & Applied Nutrition, Final Decision Letter written by Christine L. Taylor Ph.D., Phosphatidylserine and Cognitive Dysfunction and Dementia (Qualified Health Claim: Final Decision Letter), Office of Nutrition Products, Labeling and Dietary Supplements, U.S. Food & Drug Administration, May 13, 2003.
Yoko Irukayama Tomobe et al., The Activity of Docosahexaenoic Acid (DHA)-rich Phospholipid was different from that of DHA-rich Triacylglycerol in Spontaneously Hypertensive Rats, J. Oleo Sci., 2001, pp. 945-950 (also numbered pp. 25-30), vol. 50, No. 12.
Miho Itomura et al., The effect of fish oil on physical aggression in schoolchildren—a randomized, double-blind, placebo-controlled trial, Journal of Nutritional Biochemistry, 2005, pp. 163-171, vol. 16, Elsevier Inc.
B.L. Jorissen et al., The Influence of Soy-derived Phosphatidylserine on Cognition in Age-Associated Memory Impairment, Nutritional Neuroscience, 2001, pp. 121-134, vol. 4.

Katbi J. Kemper, MD, MPH, Editorials, Dietary supplements for attention-deficit/hyperactivity disorder—a fishy business?, The Journal of Pediatrics, Aug. 2001, pp. 173-174, vol. 139, No. 2.

Shlomo Keidar, Angiotensin, LDL Peroxidation and Atherosclerosis, Life Sciences, 1998, pp. 1-11, vol. 63, No. 1, Elsevier Science, Inc.

Parris M. Kidd, Ph.D., Attention Deficit/Hyperactivity Disorder (ADHD) in Children: Rationale for Its Integrative Management, Alternative Medicine Review, 2000, pp. 402-428, vol. 5, No. 5, Thorne Research, Inc.

Dominique Lemaitre-Delaunay et al., Blood compartmental metabolism of docosahexaenoic acid (DHA) in humans after ingestion of a single dose of [13C]DHA in phosphatidylcholine, Journal of Lipid Research, 1999, pp. 1867-1874, vol. 40.

Ann-Marie Lyberg et al., Monitoring the Oxidation of Docosahexaenoic Acid in Lipds, Lipds, 2005, pp. 969-979, vol. 40, No. 9.

Mark A. McDaniel et al., "Brain-Specific" Nutrients: A Memory Cure?, Psychological Science in the Public Interest, May 2002, pp. 12-38, vol. 3, No. 1, American Psychological Society.

E.A. Mitchell et al., Clinical Characteristics and Serum Essential Fatty Acid Levels in Hyperactive Children, Clinical Pediatrics, Aug. 1987, pp. 406-411, vol. 26, No. 8.

Frits A. J. Muskiet et al., Is Docosahexaenoic Acid (DHA) Essential? Lessons from DHA Status Regulations, Our Ancient Diet, Epidemiology and Randomized Controlled Trials, American Society for Nutritional Sciences, J. Nutr., 2004, pp. 183-186, vol. 134.

Ryuichi Nakashima et al., Synthesis of Didocosahexaenoylphosphatidylserine, Biosc. Biotech. Biochem., 1997, pp. 1991-1994, vol. 61, No. 12.

S. Reisbick et al., Home Cage Behavior of Rhesus Monkeys With Long-Term Deficiency of Omega-3 Fatty Acids, Physiology & Behavior, 1994, pp. 231-239, vol. 55, No. 2, Elsevier Science Ltd.

A.J. Richardson et al., The potential role of fatty acids in attention-deficit/hyperactivity disorder, Prostaglandins, Leukotrienes and Essential Fatty Acids, 2000, pp. 79-87, vol. 63 (1/2); Hardcourt Publishers Ltd.

Thomas A. Rugino, MD, et al., Effects of Modafinil in Children With Attention-Deficit/Hyperactivity Disorder: An Open-Label Study, J. Am. Acad. Child Adolesc. Psychiatry, Feb. 2001, pp. 230-235, vol. 40, No. 2.

Jin-Hyans Song et al., Oxidative Stability of Docosahexaenoic Acid-containing Oils in the Form of Phospholipids, Triacylglycerols, and Ethyl Esters, Biosc. Biotech. Biochem., 1997, pp. 2085-2088, vol. 61, No. 12.

Laura J. Stevens et al., Essential fatty acid metabolism in boys with attention-deficit hyperactivity disorder, Am. J. Clin. Nutr., 1995, pp. 761-768, vol. 62, American Society for Clinical Nutrition.

Laura Stevens et al., EFA Supplementation in Children with Inattention, Hyperactivity, and Other Disruptive Behaviors, Lipids, 2003, pp. 1007-1021, vol. 38, No. 10.

C.A. Stewart et al., The Watermaze, Behavioural Neuroscience: A Practical Approach. 1993, Shagal A. ed., pp. 107-122, vol. 1, Oxford University Press, New York, NY.

James M. Swanson et al., Effect of Stimulant Medication on Children with Attention Deficit Disorder: A "Review of Reviews", Exceptional Children, Oct. 1993, pp. 154-162, vol. 60, No. 2.

Tomoyuki Tahara et al., Stimulation of Interferon $\beta$ Production of Cultured Cells by Phospholipids in Foodstuffs, Biosc. Biotech. Bioche., 1992, pp. 1465-1466, vol. 56, No. 9.

Kaoru Tochizawa et al., Effects of Phospholipids Containing Docosahexaenoic Acid on Differentiation and Growth of HL-60 Human Promyelocytic Leukimia Cells, J. Jpn. Oil Chem. Soc., 1997, pp. 383-390, vol. 46, No. 4.

G. Toffano et al., Pharmacological Properties of Phospholipid Liposomes, Pharmacological Research Communications, 1980, pp. 829-845, vol. 12, No. 9, Italian Pharmacological Society.

Robert G. Voigt, MD, et al., A randomized, double-blind, placebo-controlled trial of docosahexaenoic acid supplementation in children with attention-deficit/hyperactivity disorder, The Journal of Pediatrics, Aug. 2001, pp. 189-196, vol. 139, No. 2.

Nobuhiro Yamamoto et al., Effect of dietary alpha-linolenate/linoleate balance on brain lipid compositions and learning ability of rats, Journal of Lipid Research, 1987, pp. 144-151, vol. 28.

Shlomo Yehuda et al., Modulation of learning, pain thresholds, and thermoregulation in the rat by preparations of free purified alpha-linolenic and linoleic acids: Determination of the optimal omega-3-to-omega-6 ratio, Proc. Natl. Acad. Sci. USA, Nov. 1993, pp. 10345-10349, vol. 90.

Genevieve S. Young et al., Effect of randomized supplementation with high dose olive, flax or fish oil on serum phospholipids fatty acid levels in adults with attention deficit hyperactivity disorder, Reprod. Nutr. Dev., 2005, pp. 549-558, vol. 45.

Office Action issued May 14, 2009 in connection with U.S. Appl. No. 11/872,258, filed Oct. 15, 2007.

Office Action issued May 14, 2009 in connection with U.S. Appl. No. 11/872,440, filed Oct. 15, 2007.

Interview Summary dated Sep. 23, 2009 issued in connection with U.S. Appl. No. 11/872,440, filed Oct. 15, 2007.

Office Action issued May 15, 2007 in connection with U.S. Appl. No. 11/414,150, filed Apr. 28, 2006.

Office Action issued Jul. 6, 2007 in connection with U.S. Appl. No. 11/414,150, filed Apr. 28, 2006.

Final Office Action issued Jan. 15, 2008 in connection with U.S. Appl. No. 11/414,150, filed Apr. 28, 2006.

Advisory Action issued May 14, 2008 in connection with U.S. Appl. No. 11/414,150, filed Apr. 28, 2006.

Office Action issued Sep. 25, 2008 in connection with U.S. Appl. No. 11/414,150, filed Apr. 28, 2006.

Office Action issued Apr. 28, 2009 in connection with U.S. Appl. No. 11/414,150, filed Apr. 28, 2006.

Interview Summary dated Aug. 11, 2009 issued in connection with U.S. Appl. No. 11/414,150, filed Apr. 28, 2006.

* cited by examiner

LIPIDS CONTAINING OMEGA-3 AND OMEGA-6 FATTY ACIDS

RELATED APPLICATION

This application is a continuation of U.S. Ser. No. 11/872,258, filed Oct. 15, 2007 now abandoned, which is a continuation of U.S. Ser. No. 10/994,175, filed Nov. 19, 2004, now abandoned, which in turn is a continuation of PCT International Application No. PCT/IL2004/000957, filed Oct. 21, 2004, the contents of each of which are hereby incorporated by reference in their entirety into this application.

BACKGROUND OF THE INVENTION

1. Field of the Invention

The present invention relates to phospholipids and polar lipids preparations which are enriched with omega-3 and/or omega-6 fatty acids covalently attached to the lipid backbone. The phospholipid preparations of the invention are particularly useful as nutraceuticals, food additives and/or pharmaceutical agents for the treatment of various conditions, in particular related to cognitive functions.

2. Prior Art

Lipids, and especially polar lipids, nitrogen containing lipids, and carbohydrate containing lipids (phospholipids, sphingosines, glycolipids, ceramides, sphingomyelins) are the major building blocks of cell membranes, tissues, etc. Additionally they play important roles in signal transduction processes and in a variety of biochemical and biosynthetic pathways.

Glycerophospholipids, lipids based on a glycerol backbone and containing a phosphate head group, are the main building blocks of cell membranes. Since most, if not all, biochemical processes involve cell membranes, the structural and physical properties of membranes in different tissues is crucial to the normal and efficient functioning of membranes in all biochemical processes.

In light of the emerging functional foods category in the area of dietary lipids many health benefits have been attributed to the consumption of certain fatty acids. For example, it has been reported in many research studies that polyunsaturated fatty acids (PUFA) of the type omega-3 and omega-6, have several health benefits on cardiovascular disease, immune disorders and inflammation, renal disorders, allergies, diabetes, and cancer. These types of fatty acids are naturally occurring mainly in fish and algae, where they are randomly distributed on the sn-1, sn-2, and sn-3 positions of the glycerol backbone of triglycerides.

The professional literature emphasizes the importance of an adequate diet containing omega-3 fatty acids. Extensive clinical studies investigating the importance of Docosahexaenoic acid (DHA), one of the most important omega-3 fatty acids, in the brain, found that low levels of DHA are associated with depression, memory loss, dementia, and visual problems. All studies showed a dramatic improvement in the elderly brain function as blood levels of DHA increased.

Other known benefits of DHA include: lower risk of arrhythmias, reduction in the risk of sudden cardiac death, lower plasma triglyceride levels and reduced blood clotting tendency. Furthermore, DHA may have importance in the field of brain functioning enhancement, baby formula fortification, diabetics and cancer. Nutritional studies, investigating the importance of DHA in the brain, found that low levels of DHA are associated with depression, memory loss, cognitive impairment, dementia and visual problems.

The human body does not adequately synthesize DHA. Therefore it is necessary to obtain it from the diet. Humans obtain DHA from their diets, initially through the placenta, then from breast milk, and later through dietary sources, such as fish, red meats, animal organ meats and eggs. Popular fish like tuna, salmon and sardines are rich sources. Until recently, the primary source of DHA dietary supplements has been fish oils. The ability of enzymes to produce the omega-6 and omega-3 family of products of linoleic and alpha-linolenic acid declines with age. Because DHA synthesis declines with age, as we get older our need to acquire DHA directly from diet or supplements increases. In fact, several recent publications suggested DHA to be considered as essential fatty acid [for example, Muskiet, F. et al. (2004) *J. Nutr.* 134(1):183-6].

Because DHA is important for signal transmission in the brain, eye and nervous system, many consumers concerned with maintaining mental acuity are searching for a pure, safe way to supplement their DHA levels.

Polyunsaturated acids, in particular long chain, such as omega-3 and 6, have been shown to confer many valuable health benefits on the population. The global market for long-chain PUFAs, including the food segment, is rapidly growing.

The majority of efforts in the industry are however invested in the improvement of PUFA processing techniques and in the creation of higher concentrated grades of PUFA derivatives to accommodate dietary supplements and functional foods needs.

The academic and industrial communities are less concerned regarding the evaluation of different delivery approaches of PUFA in order to enhance their bio-availability and their efficacy in term of their known variety of health benefits. These benefits range from prevention and treatment of CVD, diabetes, cognitive disorders and/or decline, visual disorders, skin conditions, learning disorders, etc. Additionally, PUFAs have been shown to assist in the cognitive and visual development of infants.

SUMMARY OF THE INVENTION

PUFA-lipids
PS-PUFA

Phosphatidylserine, also known as PS, is a natural phospholipid with bio-functionality that has made it one of the most promising dietary supplements in the field of brain nutrition. PS and its health benefits have been known to the scientific and nutrition communities since the 1970's. Numerous studies have been conducted in order to establish this efficacy in a variety of cognitive and mental functions. Those studies have shown that PS can improve memory, fight dementia, fight early stages of Alzheimer's disease, reduce stress and tension, improve attention span, enhance mood and fight depression, to name but few.

PS is one of the most important building blocks of cell membranes in the brain. Hence, the level of PS in brain cell membranes ensures the fluidity and structure of these membranes. The normal level ensures normal and efficient signal transduction processes, efficient glucose consumption, and other biological pathways that result in normal cognitive and mental functions.

Since PS is not abundant in human nutrition and since in many people, especially the elderly, the biosynthetic pathways responsible for the production of PS are malfunctioning, the levels of PS in the body and brain are low. This results in a variety of cognitive and mental disorders, such as depression, memory loss, short attention span, learning difficulties, etc.

The supplementation of PS in the diets of elderly people with such disorders has resulted, in many cases, in dramatic improvements of these disorders. Over the recent years, studies have shown that even younger people can benefit from dietary supplementation of PS. PS has been shown to improve the learning capabilities of students, improve memory and attention span, etc.

It is therefore an object of the present invention to provide special preparations of PS, for use mainly as nutraceuticals and as functional food additives.

PC-PUFA

As mentioned before, phospholipids are essential components of all cellular and sub-cellular membranes. Phosphatidylcholine and phosphatidylethanolamine predominate quantitatively, substantially constituting the typical bilayer configuration. Phospholipids belong to the amphipathic molecules with a water-soluble and a fat-soluble component. In the bilayer configuration the hydrophilic groups are arranged at the outer and inner side of the membrane toward the surrounding medium; the lipophilic groups, in contrast, face each other at the inner side of the bilayer configuration.

Other important constituents of biological membranes are cholesterol, glycolipids, and peripheral and integral proteins. The basic structure of biological membranes is thus a series of recurrent unities of lipid-protein complexes. The membrane is asymmetric. The function of the external (cellular) and internal (sub cellular) membrane systems depends on their composition and on the integrity of their phospholipid structure. In addition to their presence in cell membranes, phospholipids constitute structural and functional elements of the surface mono-layers of lipoproteins and of surfactants.

Of utmost importance for the function of biological membranes is their fluidity, which is decisively influenced by phospholipids. Besides the content in cholesterol and proteins and the nature and charge of the polar head groups of phospholipids in the system, membrane fluidity depends on the length of the chains of fatty acid residues in the phospholipid molecule, as well as on the number and type of pairing of their double bonds.

Phospholipids containing poly-unsaturated fatty acids supply the organism with important building blocks which improves membrane fluidity.

Studies conducted with PUFA-containing phospholipids have shown the following:
1. They are high-energy, basic, structural, and functional elements of all biological membranes, such as cells, blood corpuscles, lipoproteins, and the surfactant.
2. They are indispensable for cellular differentiation, proliferation, and regeneration.
3. They maintain and promote the biological activity of many membrane-bound proteins and receptors.
4. They play a decisive role for the activity and activation of numerous membrane-located enzymes, such as sodium-potassium-ATPase, adenylate cyclase and lipoprotein lipase.
5. They are important for the transport of molecules through membranes.
6. They control membrane-dependent metabolic processes between the intracellular and intercellular space.
7. The polyunsaturated fatty acids contained in them, such as linoleic acid, are precursors of the cytoprotective prostaglandins and other eicosanoids.
8. As choline and fatty acid donors they have an influence in certain neurological processes.
9. They emulsify fat in the gastrointestinal tract.
10. They are important emulsifiers in the bile.
11. They codetermine erythrocyte and platelet aggregation.
12. They influence immunological reactions on the cellular level.

Phospholipids containing PUFA are theoretically of importance in all those diseases in which damaged membrane structures, reduced phospholipid levels, and/or decreased membrane fluidity are present. This hypothesis is supported by experimental and clinical investigations of various membrane-associated disorders and illnesses.

Studies on the active principle as well as pharmacological and clinical trials are available on a variety of disturbances and diseases related to membrane damages. For example, in liver diseases the hepatocyte structures are damaged by, for example, viruses, organic solvents, alcohol, medicaments, drugs, or fatty food. As a consequence, membrane fluidity and permeability may be disturbed, and membrane-dependent metabolic processes as well as membrane-associated enzyme activities may be impaired. This considerably inhibits the metabolism of the liver.

Other examples include hyperlipoproteinemia with or without atherosclerosis, hemorrheological disturbances with an elevated cholesterol/phospholipid ratio in the membranes of platelets and red blood cells, neurological diseases, gastro intestinal inflammations, kidney diseases, and in a variety of aging symptoms.

All these very different diseases have in common comparable membrane disorders. With polyunsaturated phosphatidylcholine molecules such disorders may be positively influenced, eliminated, or even improved beyond normal due to the high content in polyunsaturated fatty acids. Following are some examples of the mechanisms that mediate this phenomenon:
1. HDL particles enriched with PUFA-containing-phosphatidylcholine are able to take up more cholesterol from low-density lipoprotein (LDL) and tissues. More cholesterol can be transported back to the liver. This action on the cholesterol reverse transport is unique. All other lipid-lowering agents reduce either the cholesterol absorption in the body or the cholesterol synthesis in the liver and its distribution to the periphery. These substances, however, do not physiologically mobilize the cholesterol already present in the periphery.
2. The cholesterol/phospholipid ratio in membranes, platelets, and red blood cells decreases and membrane function is improved up to normalization.
3. Peroxidative reactions are reduced, damaged hepatocyte membrane structures restored, membrane fluidity and function stabilized, immuno-modulation and cell protection improved, and membrane-associated liver functions enhanced.
4. With the normalization of the cholesterol/phospholipid ratio, the bile is also stabilized.
5. Due to its specific property as a surface-active emulsifier, PUFA-containing-phosphatidylcholine solubilize fat and is used in reducing the risk and treatment of fat embolism.
6. The substitution with poly-unsaturated-fatty-acids and choline may have a cytoprotective effect in the brain and activate neuronal processes.
7. Liposomes with polyunsaturated phosphatidylcholine molecules may act as drug carriers, such as of vitamin E.

Liver Disease

Experimental and clinical results support the assumption that the therapeutic application of PUFA-containing-phosphatidylcholine has protective and even curative and regenerative effects on biological membranes of sinus endothelial cells and hepatocytes. The cytoprotective effect of PUFA-containing-phosphatidylcholine has been corroborated in 7 in vitro and in 55 in vivo experiments, in which 20 different models with five different animal species were used. Types of intoxication that are known to play a role in the etiology of liver disease have mostly been applied: chemical substances, medicaments, alcohol, cholestasis, immunological phenomena, exposure to radiation, and so on.

The hepato-protective effects of PUFA-containing-phosphatidylcholine have been confirmed and were the more pronounced the earlier PUFA-containing-phosphatidylcholine was administered:
1. Structures of membranes were normal or largely normalized.
2. Fatty infiltrations and hepatocyte necrosis could be diminished or even eliminated.
3. Corresponding data were found for lipid peroxidation, transaminase and cholinesterase activity, and for serum lipids; liver cell metabolism increased.
4. The increase of RNA and protein synthesis and of the liver cell glycogen content indicated a stimulation of the liver cells.
5. Reduced collagen production, collagen/DNA ratio, and liver hydroxyproline content indicated a reduced formation of connective tissue.

The dosage of PUFA-containing-phosphatidylcholine ranged from 525 to 2,700 mg/day when administered orally, and from 500 to 3,000 mg/day in intravenous application. The duration of treatment lasted from a few weeks to up to 30 months. The main liver indications were acute hepatitis, chronic hepatitis, fatty liver, toxic liver damage, cirrhosis of the liver, and hepatic coma.

The clinical findings, showing the effectiveness of PUFA-containing-phosphatidylcholine, can be summarized generally as follows:
1. Accelerated improvement or normalization of subjective complaints, of clinical findings, and of several biochemical values
2. Better histological results as compared with the control groups
3. A shortened duration of hospitalization Promising results were obtained also in renal disorders, chronic ambulatory peritoneal dialysis, hyperlipoproteinemia/atherosclerosis, gastrointestinal inflammation, psoriasis, and more.

Recent research studies have shown that PUFA-enriched phospholipids, isolated from rainbow trout embryos, have novel health benefits. Some of these benefits include the treatment of tumor cells, inhibition of 5-lipoxygenase activity, reduction of neutral fat levels (such as cholesterol).

There is proof that a person who receives enriched phospholipids nutritionally, these phospholipids cross the intestinal barrier and the blood-brain barrier, thus reaching the brain. Recently, investigators from Ponroy Laboratories had described an experiment in which mice lacking essential fatty acids, i.e. linoleic acid (18:2 n-6) and α-linolenic acid (18:3 n-3), which serve as the sole sources for LC-PUFA, were fed cerebral phospholipids and the quantity of phospholipids in each part of the brain measured. These phospholipids were found in the cytoplasm, in the synapses, and in other parts of the brain [Carrie et al., (2000) J. Lipid Res. 41, 465-472].

The utilization of phospholipids enriched with PUFA holds many potential advantages from a clinical point of view. The phospholipid may deliver the essential fatty acid to specific organs or body parts, such as the brain, and assist in the incorporation of these fatty acids in membranes. Other advantages may arise from the fact that phospholipids enriched with PUFA will not have odor problems such as found in the major current nutraceutical source, the fish oils. Furthermore, some preliminary clinical studies have shown that PUFA incorporated in phospholipids possess superior efficacy than PUFA carried by triglycerides. [Song et al. (2001) *Atherosclerosis*, 155, 9-18].

Further studies have shown that the activity of DHA-rich phospholipid was different from that of DHA-rich triacylglycerol in spontaneously hypertensive rats [Irukayama-Tomobe et al. (2001) *Journal of Oleo Science*, 50(12), 945-950]. Spontaneously hypersensitive rats (SHR) were fed test lipid diets for six weeks, which contained 30%-docosahexaenoic acid (DHA) phospholipid (DHA-PL) extracted from fish roe or 30%-DHA fish oil (DHA-TG). The control diet contained corn oil in the presence of test lipids. After feeding, blood pressure in the DHA-TG and DHA-PL diet groups was found significantly lower compared to the control. Serum fatty acid content of dihomo-linoleic acid (DHLnA) and Arachidonic acid (AA) of the DHA-PL diet group was significantly less than the control or DHA-TG diet group. Serum triacylglycerol, phospholipid and total cholesterol in the DHA-TG and DHA-PL diet groups were significantly less than in the control. Liver total cholesterol in DHA-PL was twice that in the DHA-TG diet group and control. The mechanism for cholesterol removal from blood by DH-PL would thus appear to differ from that by DHA-TG. Serum lipid peroxide (LPO) in the DHA-TG and DHA-PL diet groups was essentially the same as in the control.

Many PUFA-containing agents suffer from stability and quality problems due to the high degree of oxidation of the polyunsaturated fatty acids. These problems require the incorporation of antioxidants as well as the utilization of special measures which attempts to reduce this oxidation. The utilization of phospholipids as carriers of PUFA may result in enhanced stability of such products due to the anti-oxidative properties of phospholipids.

It seems that one of the most effective transport mechanism for such essential fatty acids is the attachment of these groups to phospholipid molecules. The phospholipids have been shown to pass through the blood-brain barrier and transport the DHA where it is needed.

Organoleptic Concerns

PUFAs are traditionally extracted from coldwater fish. Despite the healthy image, one of the problems of consumer acceptance has been the resulting strong, fishy taste. To address this, microencapsulated forms of omega-3 have been pioneered in the last 15 years. A further step was the development of egg-containing products such as DHA-enriched mayonnaise and pasta. DHA-enriched yogurts, baked goods and broilers were also envisaged.

There is no other nutritional product or ingredient that is considered to be an agent of PUFA delivery. All current commercial products are based on the fatty acids themselves in an encapsulated form or on foods enriched with PUFA through special animal/crop feed.

It is therefore an object of the present invention to provide lipid preparations enriched with omega-3 or omega-6 fatty acids, for use mainly as nutraceuticals and as functional food additives. The composition of said preparation is such that it provides the preparation with the property of enhancing the bioavailability of PUFAs. Thus upon its consumption, preferably in the form of nutraceuticals, food additives or pharmaceutical compositions, the organism may, in the most efficient way, enjoy the benefits provided by said preparation, as will be described in detail below.

This and other objects of the invention will become apparent as the description proceeds.

In a first aspect the present invention provides a lipid preparation, wherein said lipid is selected from glycerophospholipids and their salts, conjugates, and derivatives and any mixture thereof, and poly-unsaturated fatty acid (PUFA) acyl groups, particularly long-chain poly-unsaturated fatty acid (LC-PUFA) acyl groups, preferably omega-3 and/or omega-6 acyl groups, at a concentration of least 5% (w/w) of total fatty acids content of said preparation, preferably more than 10% (w/w), more preferably 20-50% (w/w), wherein said PUFA is covalently bound to said lipid.

Said lipid may be a naturally occurring lipid, or a synthetic lipid. Preferably, said lipid is a glycerophospholipid in which at least some of the sn-1 or sn-2 groups of the glycerol backbone are substituted with said poly-unsaturated fatty acid (PUFA) acyl groups.

In one particular embodiment, said lipid is a glycerophosphlipid of formula I:

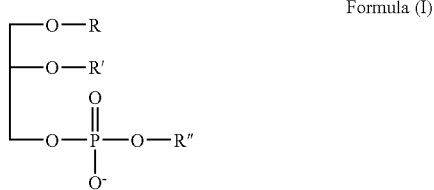

Formula (I)

wherein R" represents a moiety selected from serine (PS), choline (PC), ethanolamine (PE), inositol (PI), glycerol (PG) and hydrogen (phosphatidic acid—PA), and R and R', which may be identical or different, independently represent hydrogen or an acyl group, wherein said acyl group is selected from saturated, mono-unsaturated or poly-unsaturated acyl groups (PUFA), particularly long-chain poly-unsaturated fatty acids (LC-PUFA), more preferably omega-3 and/or omega-6 acyl groups, and salts thereof, with the proviso that R and R' cannot simultaneously represent hydrogen, and wherein said polyunsaturated acyl groups comprise at least 5% (w/w) of total lipid fatty acids, preferably more than 10% (w/w), and particularly 20-50% (w/w).

In one more particular embodiment of said preparation, R represents hydrogen and R' represents an acyl group. Alternatively, R' represents hydrogen and R represents an acyl group.

Considering these latter embodiments, when said acyl group is preferably an omega-3 acyl group, it may be an eicosapentaenoyl (EPA), a docosahexaenoyl (DHA) group, or linolenic omega-3 group. And, when said acyl group is preferably an omega-6 acyl group, it may be an arachidonoyl (ARA) group, or a linoleic omega-6 group. A further possibility is that said acyl group may be a linolenoyl (18:3) group.

In a yet further embodiment of the preparation of the invention, R" may be any one of serine, choline, ethanolamine, inositol or glycerol.

In a further particular embodiment, the identity and content of R and R' are predetermined.

The preparation of the invention which comprises the compound of formula I in which R" is serine, mimics the composition of human brain PS.

Nonetheless, the invention also refers to preparations comprising the compound of formula I in which R" is serine, which are different from human brain PS, but still have an improved bioactivity, particularly as compared to soybean-PS. This improved bioactivity results in beneficial effects on both the learning and working memory in elderly population, in particularly in cholinergic impaired conditions like Alzheimer's disease.

The invention also relates to preparation PS preparation which mimics the human brain PS, is effective at lower dosage (2-3 fold) compared to soybean-PS, while having similar or improved bioactivity compared to soybean-PS.

The PS may be of plant, animal or microorganism source, and is enriched with PS of formula I, wherein R" represents a serine moiety.

The preparation of the invention may be further enriched with PS of formula I, characterized in having reduced or absent of fish-related organoleptic effects. Such preparation may be particularly suitable for incorporation into chocolate-containing or dairy-based food articles (including concentrated milk).

The preparation of the invention may be used in the improvement and treatment of cognitive and mental conditions and disorders as well as the maintenance of normal functions of brain-related systems and processes, preferably ADHD, aging, Alzheimer's disease, Parkinson's disease, multiple sclerosis (MS), dyslexia, depression, learning capabilities, intensity of brain waves, stress, anxiety, mental and psychiatric disorders, concentration and attention, mood, brain glucose utilization, general cognitive and mental well being, neurological disorders and hormonal disorders.

The preparation of the invention is particularly useful in enhancing the bioavailability of omega-3 and omega-6 fatty acids.

The preparation of the invention may be used in combined improvement of cognitive and mental functions together with improvement of additional health disorders or conditions. Such additional health disorders or conditions may be at least high blood cholesterol levels, high triglycerides levels, high blood fibrinogen levels, HDL/LDL ratio, diabetes, metabolic syndrome, menopausal or post-menopausal conditions, hormone related disorders, vision disorders, inflammatory disorders, immune disorders, liver diseases, chronic hepatitis, steatosis, phospholipid deficiency, lipid peroxidation, dysrhythmia of cell regeneration, destabilization of cell membranes, coronary artery disease, high blood pressure, cancer, hypertension, aging, kidney disease, skin diseases, edema, gastrointestinal diseases, peripheral vascular system diseases, allergies, neurodegenerative and psychiatric diseases.

The preparation of the invention may also be used in the reduction and/or prevention of serum oxidative stress leading to atherosclerosis, cardiovascular disorders and/or coronary heart disease.

The invention further relates to nutraceutical compositions comprising a lipid preparation in accordance with the invention. The nutraceutical composition may be in the form of softgel capsules, tablets, syrups, or any other common dietary supplement delivery system.

Still further, the invention relates to functional food article comprising the lipid preparation of the invention. Such functional food article may be selected from dairy products, dairy drinks, ice-creams, bakery products, confectionary products, biscuits, soy products, pastry and bread, sauces, condiments, oils and fats, margarines, spreads, cereals, drinks and shakes, oils and fats, infant formulas, infant foods (biscuits, mashed vegetables and fruits, cereals), bars, snacks, candies and chocolate products.

In yet a further aspect, the invention relates to pharmaceutical compositions comprising the lipid preparation of the invention, and optionally further comprising at least one pharmaceutically acceptable additive, diluent or excipient. The pharmaceutical composition of the invention may further optionally comprise at least one pharmaceutically active agent.

Latency time to platform in the three days of acquisition (2 sessions per day) of aged rats supplemented for three months with various supplements as detailed below was analyzed using video camera, with (open squares) or without (closed circuits) pretreatment of 1 mg/kg of scopolamine.

Figure 1A:
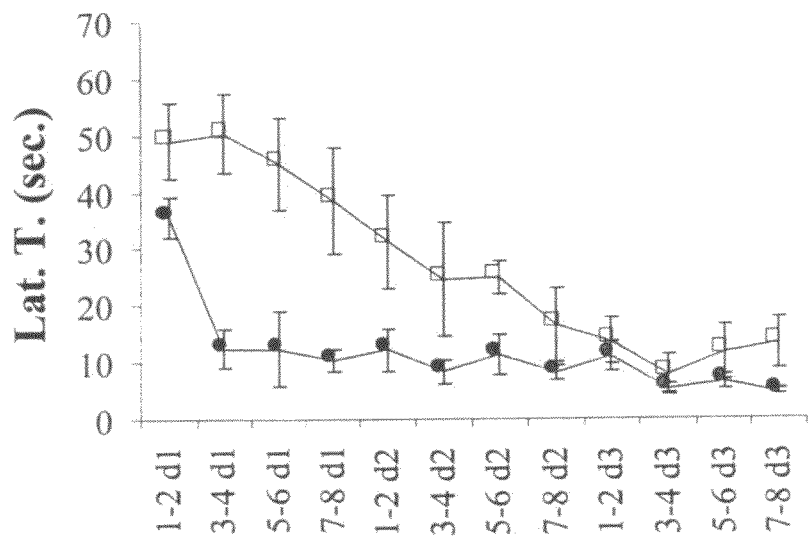
FIGS. 1A-D: Performance of rats in acquisition of the spatial Morris maze task.
Figure 1B:
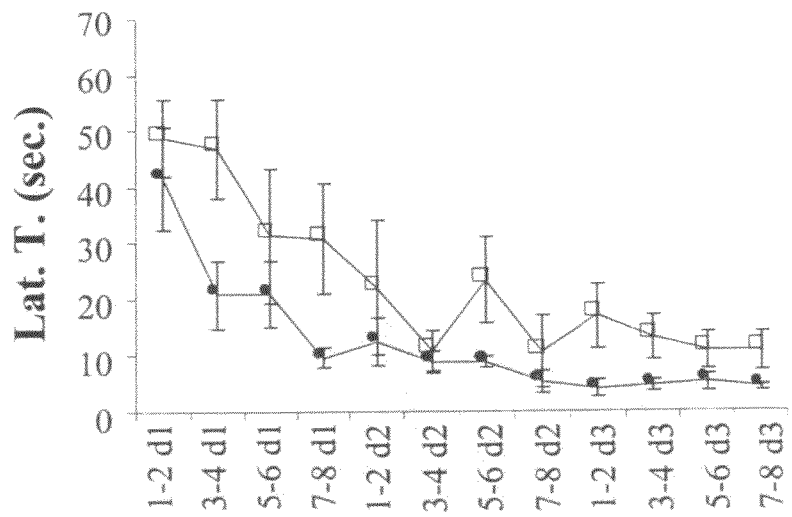
Figure 1C:
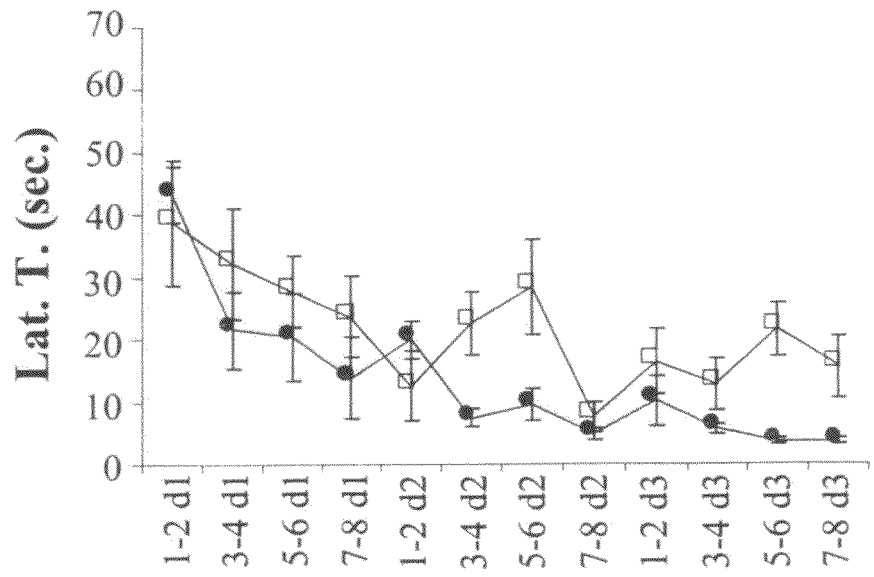
Figure 1D:
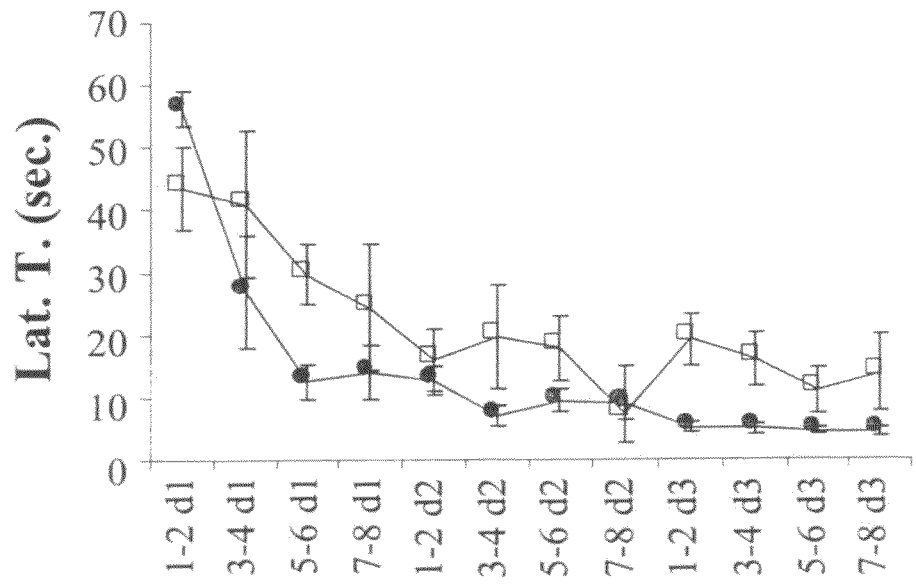

FIG. 1A: Rats supplemented with MCT, P<0.007.
FIG. 1B: Rats supplemented with PS-ω3 P<0.07.
FIG. 1C: Rats supplemented with SB-PS, P<0.02.
FIG. 1D: Rats supplemented with LC-PUFA, P<0.03.

Values represent mean±S.E.M of four to five rats per supplement.

Abbreviations: Lat. T., latency time; sec., seconds.

Figure 2:
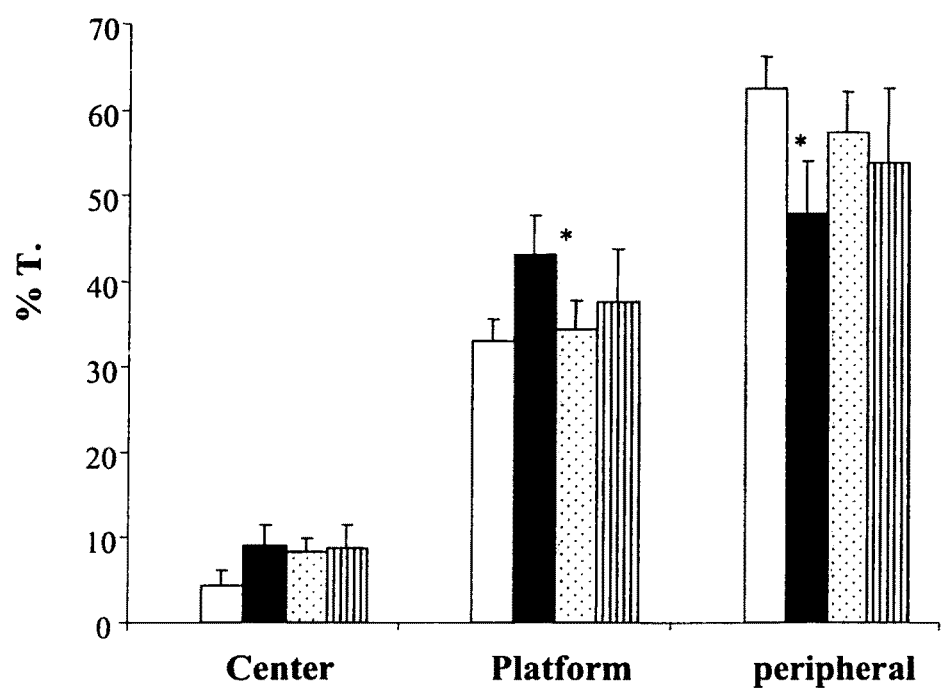

FIG. 2. Performance of scopolamine-treated rats in the Morris water maze task in the spatial probe test.

This graph represents percentage of time (T.) that aged rats, supplemented for three months with MCT (open bars), PS-ω3 (solid bars), SB-PS (dotted bars) or LC-PUFA (striped bars), spent in different areas after the platform being removed, was analyzed using video camera, following pre-treatment of 1 mg/kg of scopolamine. Values represent mean±S.E.M of four to five rats per supplement. Significance compared to control group (MCT) *P<0.02 and **P<0.08

FIGS. 3A-D: Performance of scopolamine-induced rats in locating the platform after its reposition.

Latency time to platform on the fifth day of the water maze test, in which the platform was repositioned between the sessions, in aged rats supplemented for three months with different supplements as specified below, was analyzed using video camera, with (open squares) or without (closed circuits) pretreatment of 1 mg/kg of scopolamine.

Figure 3A:
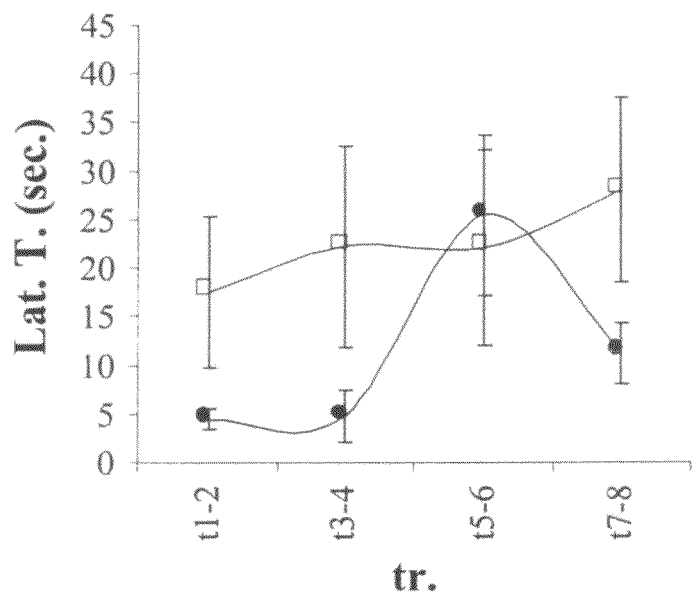
Figure 3B:
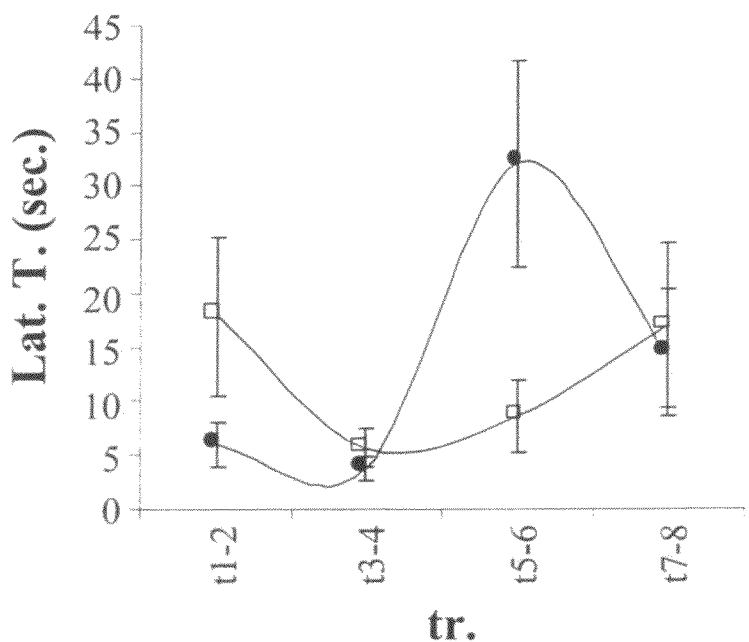
Figure 3C:
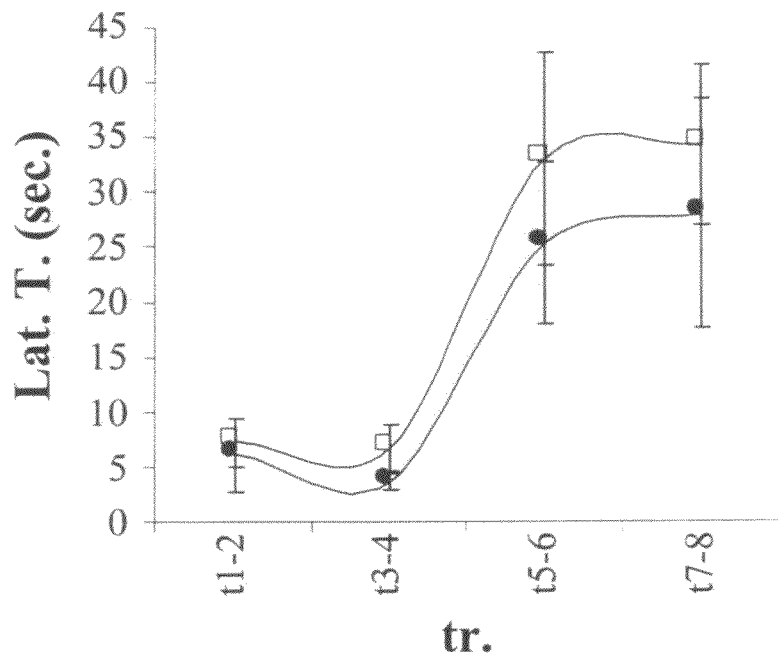
Figure 3D:
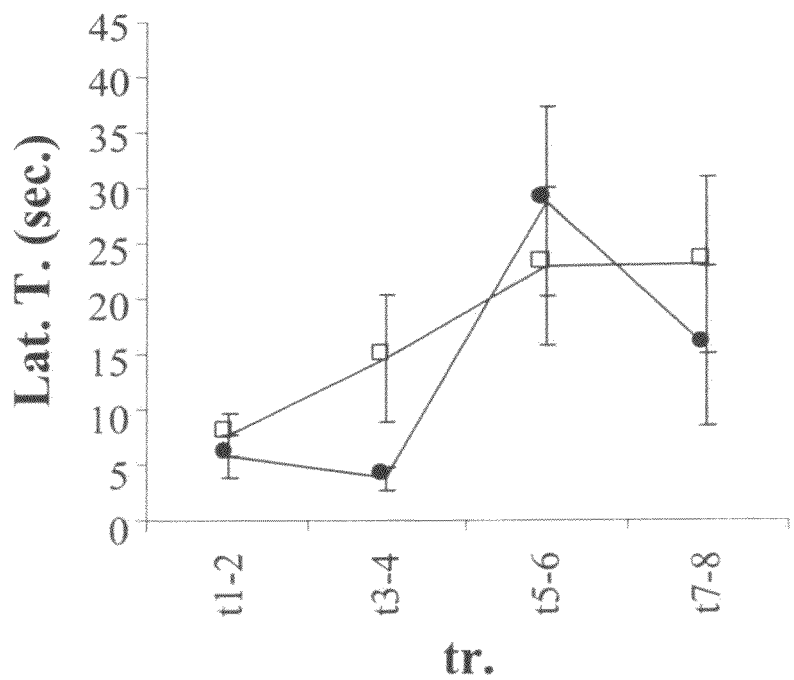

FIG. 3A: Rats supplemented with MCT.
FIG. 3B: Rats supplemented with PS-ω3.
FIG. 3C: Rats supplemented with SB-PS.
FIG. 3D: Rats supplemented with LC-PUFA.

Values represent mean±S.E.M of four to five rats per supplement.

Abbreviations: Lat. T., latency time; sec., seconds; tr., trials.

Figure 4A:
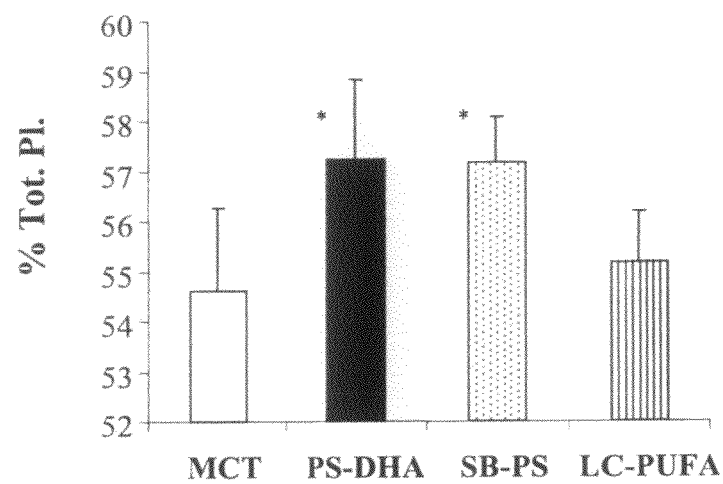
Figure 4B:
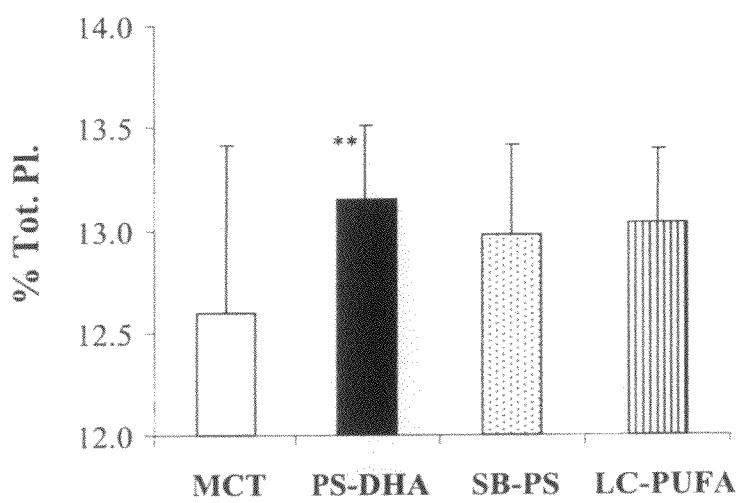

FIGS. 4A-B: Phospholipid levels in rat tissues as measured using $^{31}$P-NMR.

Lipids were extracted from tissues of aged rats that were supplemented for three months with MCT (open bars), PS-ω3 (solid bars), SB-PS (dotted bars) or LC-PUFA (striped bars). Phospholipids levels were analyzed using a $^{31}$P-NMR machine and the relative levels of phosphatidylcholine of the different treatments are presented.

FIG. 4A: Analysis of lipids extracted from the liver.
FIG. 4B: Analysis of lipids extracted from the brain (cortex region).

Values represent mean±S.D. of four to five rat tissues per supplement. Significance compared to control group (MCT) *P<0.05 and **P<0.1.

Abbreviations: Tot. Pl., total phospholipids.

Figure 5:
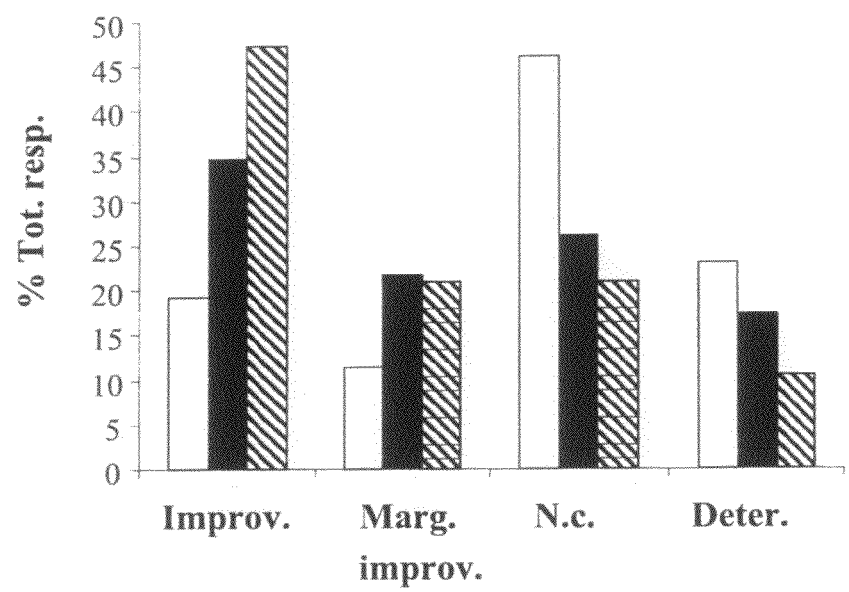

FIG. 5: Parental scores of ADHD children according to behavioral rating scales.

The graph represents percentage of ADHD children that demonstrated improvement or lack of improvement in a parental view following two months of supplementation with canola oil (open bars), DHA (solid bars) or PS-ω3 (hatched bars). Rating includes remarks regarding behavioral tendencies at home, at school, with siblings or peers and teachers feedback. Values represent percentage of twenty to twenty-five ADHD children scores per supplement. Note that twelve parents decline to respond to the questioner and six children did not complete the supplementation period due to poor taste or severe discipline problems (mostly the control group).

Abbreviations: Improv., improvement; Marg. Improve., marginal improvement; n.c., no change; Deter., deterioration.

Figure 6:
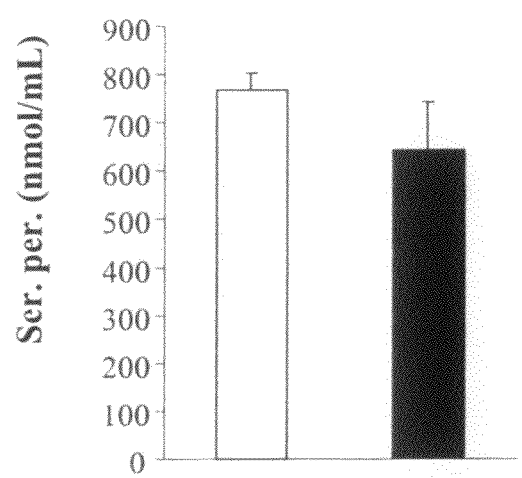

FIG. 6: Effect of PC-DHA on the serum oxidative stress.

Apo E° mice were fed for 10 weeks with placebo (open bars) or PC-DHA (solid bars). Serum lipid peroxide (Ser. per.) levels were measured using a spectrophotometric assay. Values represent mean±S.D. of 5 mice per treatment.

DETAILED DESCRIPTION OF PREFERRED EMBODIMENTS OF THE INVENTION

In a first aspect the present invention provides a lipid preparation, wherein said lipid is a glycerophospholipid, a salt, conjugate, and derivative thereof, and any mixture thereof, and poly-unsaturated fatty acid (PUFA) acyl groups, particularly long-chain poly-unsaturated fatty acid (LC-PUFA) acyl groups, preferably omega-3 and/or omega-6 acyl groups, at a concentration of at least 5% (w/w) of total fatty acids content of said preparation, preferably more than 10% (w/w), more preferably 20-50% (w/w), wherein said PUFA is covalently bound to said glycerophospholipid.

Said lipid may be a naturally occurring lipid, or a synthetic lipid.

Preferably, said lipid is a glycerophospholipid in which at least some of the sn-1 or sn-2 groups of the glycerol backbone are substituted with said poly-unsaturated fatty acid (PUFA) acyl groups.

In one particular embodiment, said lipid is a glycerophosphlipid of formula I:

$$\begin{array}{c} \text{—O—R} \\ \text{—O—R'} \\ \text{—O—}\overset{\overset{\displaystyle O}{\|}}{\underset{\underset{\displaystyle O^-}{|}}{P}}\text{—O—R''} \end{array} \qquad \text{Formula (I)}$$

wherein R" represents a moiety selected from serine (PS), choline (PC), ethanolamine (PE), inositol (PI), glycerol (PG) and hydrogen (phosphatidic acid—PA), and R and R', which may be identical or different, independently represent hydrogen or an acyl group, wherein said acyl group is selected from saturated, mono-unsaturated or poly-unsaturated acyl groups (PUFA), particularly long-chain poly-unsaturated fatty acids (LC-PUFA), more preferably omega-3 and/or omega-6 acyl groups, and salts thereof, with the proviso that R and R' cannot simultaneously represent hydrogen, and wherein said polyunsaturated acyl groups comprise at least 5% (w/w) of total lipid fatty acids, preferably more than 10% (w/w), and particularly 20-50% (w/w).

In one more particular embodiment of said preparation, R represents hydrogen and R' represents an acyl group. Alternatively, R' represents hydrogen and R represents an acyl group.

Considering these latter embodiments, when said acyl group is preferably an omega-3 acyl group, it may be an eicosapentaenoyl (EPA), a docosahexaenoyl (DHA) group, or linolenic omega-3 group. And, when said acyl group is preferably an omega-6 acyl group, it may be an arachidonoyl (ARA) group, or a linoleic omega-6 group. A further possibility is that said acyl group may be a linolenoyl (18:3) group.

In a yet further embodiment of the preparation of the invention, R" may be any one of serine, choline, ethanolamine, inositol or glycerol.

In a further particular embodiment, the identity and content of R and R' are predetermined.

The preparation of the invention which comprises the compound of formula I in which R" is serine, mimics the composition of human brain PS.

Nonetheless, the invention also refers to preparations comprising the compound of formula I in which R" is serine, which are different from human brain PS, but still have an improved bioactivity, particularly as compared to soybean-PS.

Traditionally, PS active ingredients used as dietary supplements were produced by the extraction of animal brains, particularly bovine brains. The PS extracted from animal brain tissues, similarly to human brain PS, has a fatty acid composition which is characterized by relatively higher levels of omega-3 moieties, compared to the levels of omega-3 found in plant phospholipids.

PS has the following structure:

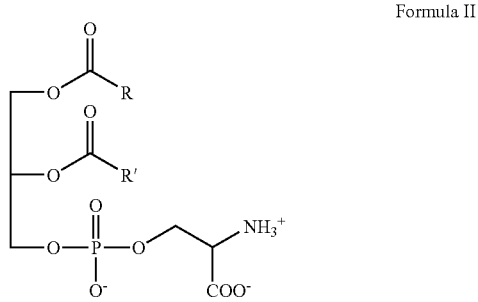

Formula II

Human brain PS is characterized by over 20-30% PS containing omega-3 fatty acyls, preferably at the sn-2 position of the glycerol moiety, and mainly DHA or EPA. As mentioned above, phospholipids, and PS in particular, are responsible for membrane structure and physical properties. One of the major physical properties governed by phospholipids is the fluidity of these membranes. Omega-3 fatty acids, DHA and EPA in particular, also have a crucial role in membrane fluidity in light of their unique 3D structure. Therefore, PS with omega-3 fatty acyl moieties, DHA and EPA in particular, has unique bio-functionality which cannot stem from just the basic phospholipid skeleton of this phospholipid.

Considering the risks involved with prion diseases, particularly bovine spongiform encephalopathy (BSE), as well as other disadvantages associated with ingredients obtained from animal sources, PS supplements are usually prepared using PS originating from soybean lecithin. This lecithin is enriched, usually enzymatically, with PS. This method of production results in PS with a fatty acid profile of soybean phospholipids, which is characterized by low level of omega-3 fatty acids, and almost no DHA and EPA. This PS active ingredient is also known as soybean-PS.

Although the bio-functionality of soybean-PS in the improvement of cognitive function has been shown to be similar to that of bovine-PS, it is still different from human brain PS. It is a purpose of the present invention to provide a PS ingredient with a predetermined fatty acid composition that mimics the fatty acid composition of the human brain PS.

It is a further object of the present invention to provide a PS ingredient which, while not identical to naturally occurring brain PS, is characterized by improved functionality, particularly in comparison with soybean-PS. This improved PS ingredient has a predetermined fatty acid composition.

The PS ingredient of the present invention is enriched with omega-3 fatty acyls, preferably DHA, EPA or linolenic omega-3. Furthermore, the PS of this invention is enriched with omega-3 fatty acyls covalently bonded to either or both of the sn-1 or sn-2 positions of the glycerol moiety in the PS backbone.

The present invention is also related and describes other phospholipids, such as phosphatidylcholine (PC), phosphatidylethanolamine (PE), phosphatidyl-inositol (PI), phosphatidylglycerol (PG) and phosphatidic acid (PA), enriched with omega-3 fatty acids, preferably DHA, EPA, or linolenic acid which are covalently bonded at either or both of the sn-1 or sn-2 positions of the glycerol moiety of the phospholipid. Alternatively, the phospholipids of the invention are enriched with omega-6 fatty acids.

When referring to PS in the present description, it should be taken to mean also any other lipid, such as, but not limited to, the polar lipids listed above.

In a preferred embodiment, the amount of omega-3 (particularly EPA, DHA or linolenic acid) or omega-6 (particularly ARA and linoleic acid) fatty acids in the PS ingredient of the invention is greater than 10% at either or both of the sn-1 or sn-2 positions, preferably at the sn-2 position, preferably over 20% and most preferably above 40%.

As mentioned, the desired omega-3/omega-6 fatty acyls can be bonded at both or only one of the sn-1 and sn-2 positions.

The fatty acid composition of the PS preparation of this invention can have a predetermined fatty acid composition similar to or different from the fatty acid composition found in normal healthy human brain, provided it has enhanced activity, particularly compared to the activity of plant PS, for example soybean-PS.

The preparation of the omega-3/omega-6-enriched PS preparation of this invention can be enzymatic, chemical or by molecular biology methods. Briefly, the PS can be enriched with omega-3 or omega-6 moieties by enzymatic processes, e.g. enrichment of a natural phospholipid/lecithin with omega-3 fatty acids by enzymatic transesterification/esterification followed by transformation of the head group to serine (using PLD enzymes) to obtain a PS-omega-3/omega-6 conjugate. Another enzymatic pathway is to obtain a lecithin or phospholipid source which is naturally rich in omega-3 acids, such as krill phospholipids, and transform their head groups to serine. It is to be noted that the fatty acid composition of the PS obtained by this method has an omega-3 composition which is predetermined by the source of choice (fish, krill, algae, etc.). Such methods have been thoroughly described in Applicant's co-pending PCT Application claiming priority from IL158553.

The PS-omega-3/omega-6 ingredient of the present invention can also be prepared by chemical transesterification/esterification methods that will enrich the sn-1 and 2 positions with omega-3 or omega-6 acyl residues. Such methods of preparation of PS-omega-3 and PS-omega-6 have been described in Applicant's co-pending PCT Application claiming priority from IL158553.

Alternatively, the PS ingredient of the present invention can be prepared by GMO (genetically modified organisms)/biotechnology methods, for example, providing phospholipids-producing organisms with omega-3 or omega-6 fatty acids to obtain phospholipids enriched with omega-3 or omega-6 PS. It may be preferred to use genetically engineered plants or microorganisms, to avoid use of animal sources.

The PS of this invention can have the omega-3 or omega-6 fatty acid composition of a specific lecithin raw material, relatively rich with omega-3 or omega-6 fatty acids, enriched with PS to yield a PS ingredient with elevated omega-3 or omega-6 fatty acids levels, compared to soybean-PS. Such is the case, for example, when phospholipids from krill are used as the starting material, as described above.

In a preferred embodiment the PS enriched with omega-3 or omega-6 can be soybean-PS or any other PS, from plant, animal, for example krill, or microorganism source. In a further preferred embodiment the omega-3 or omega-6 enrichment can be performed on a lecithin, which in turn is enriched with PS by transphosphatidylation.

It is the purpose of this invention to provide a novel PS ingredient, enriched with omega-3 fatty acids, resulting in an ingredient with improved efficacy compared to ingredients containing natural or simply enriched PS.

The improved PS preparation of this invention exhibits enhanced activity in the improvement and treatment of cognitive and mental conditions and disorders as well as the maintenance of normal functions of brain related systems and processes. These include, but are not limited to ADHD, multiple sclerosis (MS), dyslexia, depression, learning capabilities, intensity of brain waves, stress, mental and psychiatric disorders, neurological disorders, hormonal disorders, concentration and attention, mood, brain glucose utilization, and general cognitive and mental well being.

The novel lipid preparation of this invention exhibits enhanced activity in the improvement of cognitive functions, as detailed hereunder, over omega-3 or omega-6 lipids per se or soybean-PS. Furthermore, under certain conditions or for all or specific disorders, the lipid preparation of the invention is effective at a dosage of less than 100 mg/day. This is lower that the current recommended daily dosage of soybean-PS (100-300 mg/day) or omega-3 lipids (approx. 1-2 g/day or more) currently available in the market. Nonetheless, dosages of 100-600 mg/day are preferred for enhanced efficacy of the lipid preparation of the invention.

An important advantage of the PS preparation of the invention is that it exhibits multifunctional activity. This multi-functionality is exhibited by improvement in cognitive and mental functions, together with improvement of other health disorders or conditions.

The enhanced activity of this PS ingredient, as well as its multi-functionality, may arise from the unique structure of this ingredient and its influence on the physical and chemical properties of cell membranes in brain tissues as well as other organs and tissues.

The enhanced activity of this PS ingredient, as well as its multi-functionality, may also be attributed to the enhanced bioavailability of the omega-3 fatty acids, due to their incorporation in the PS skeleton. Thus, the omega-3 fatty acids can be delivered to the brain across the blood-brain barrier, being a part of the PS molecule, which readily passes this barrier. The PS functions as a delivery platform for the fatty acids bound thereto, to various organs and tissues, thereby enhancing their bioavailability.

The additional health disorders or conditions which are affected by the multifunctional PS preparation of the invention include, but are not limited to high blood cholesterol levels, high triglycerides levels, high blood fibrinogen levels, HDL/LDL ratio, diabetes, metabolic syndrome, menopausal or post-menopausal conditions, hormone related disorders, vision disorders, inflammatory disorders, immune disorders, liver diseases, chronic hepatitis, steatosis, phospholipid deficiency, lipid peroxidation, dysrhythmia of cell regeneration, destabilization of cell membranes, coronary artery disease, high blood pressure, cancer, hypertension, aging, kidney disease, skin diseases, edema, gastrointestinal diseases, peripheral vascular system diseases, allergies, airways diseases, neurodegenerative and psychiatric diseases.

The new ingredients of the invention can be delivered and utilized in a variety of products. Such products include dietary supplements, functional foods, pharmaceutical delivery systems, etc.

The preparation of pharmaceutical compositions is well known in the art and has been described in many articles and textbooks, see e.g., Gennaro A. R. ed. (1990) *Remington's Pharmaceutical Sciences*, Mack Publishing Company, Easton, Pa., and especially pages 1521-1712 therein.

As dietary supplements, the preparations of the invention may be used in the form of soft gel capsules, tablets, syrups, and other common dietary supplements delivery systems.

As functional foods, the preparations of the invention can be incorporated and used in a variety of foods, such as dairy products, ice-creams, biscuits, soy products, pastry and bread, sauces, condiments, oils and fats, margarines, spreads, cereals, drinks and shakes, infant formulas, infant foods (biscuits, mashed vegetables and fruits, cereals), bars, snacks, candies, chocolate products.

As pharmaceutical products, the preparations of the invention can be delivered orally, intravenously, or by any other conventional or special route of administration.

The new preparations of the invention may be in the form of fluid oil, powder, granules, wax, paste, oil or aqueous emulsion, and any other form that will enable its use in the target applications.

Pharmaceutical or nutraceutical formulations comprising the PS preparation of the invention may include physiologically acceptable free flowing agents, other additives, excipients, dessicants and diluents, colorants, aroma and taste ingredients, and any ingredients that control physical, organoleptic, and other properties, as well as additional active ingredients, for example minerals, vitamins, other nutritional additives.

The utilization of omega-3 lipids in a variety of applications, and especially as ingredient of functional foods, is hindered due to their distinct fish odor. Thus, another advantage of the omega-3 enriched phospholipids ingredients of the invention is that they have reduced odor or taste of omega-3 acyl moieties, due to the covalent binding of these groups to the PS backbone. This increases the vapor pressure of these materials, hence reducing their distinct aroma. Thus, the covalent binding of the omega-3 fatty acids to the phospholipid backbone, especially PS, alters and improves their taste properties. Moreover, the PS ingredient of the invention also offers enhanced stability to the oxidation sensitive omega-3 fatty acids. Phospholipids in general, and PS in particular, are known to act as anti-oxidants and stabilizers.

These benefits make the lipid preparation of the invention highly beneficial and important in a variety of applications and especially in functional foods, where stability, aroma and taste are fundamental requirements.

Furthermore, these novel ingredients can be formulated with additional lipids for an even enhanced bio-functionality and efficacy.

The polar lipids derivatives of PUFA, such as the PS-PUFA derivatives have exhibited high stability as a preparation and additionally in several food applications, used in the clinical trials of the present invention. The stability of these sensitive compounds is emerging from the covalent combination of phospholipids, known in the past to be used as preservatives and of the un-stable PUFA moieties.

The new ingredients of the invention can be delivered and utilized in a variety of products. Such products include dietary supplements, functional foods, pharmaceutical delivery systems, etc.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following Examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Example 1

Methods:
Animals and Diet

Male Wistar rats originated from the same colonies were obtained from Harlen. Fifty rats were randomly divided into five dietary supplemented groups, in addition to their normal diet: (i) a group fed 0.1 g medium-chain triglycerides (MCT)/1 ml supplement matrix (MCT group); (ii) a group fed 0.1 g DHA/EPA (20/30% of total fatty acids composition, diluted with MCT to generate 30% (w/w) LC-PUFA compound) triglycerides/1 ml supplement matrix (LC-PUFA group); (iii) a group fed 0.1 g soybean lecithin-derived PS (20% SB-PS w/w)/1 ml supplement matrix (SB-PS group); and (iv) a group fed 0.1 g PS-ω3 (20% PS w/w, and total LC-PUFA composition of 30%)/1 ml supplement matrix (PS group). The supplement matrices were stored at −20° C., and fresh portions were fed to the rats every day. AD supplements were handled so as to minimize oxidation of the fatty acids. Rats consumed the diet and water ad libitum. All rats were housed in a standard environment, in which temperature was maintained at 24±0.5° C., and the relative humidity was kept at 65±5% with 12-h periods of light and dark. Body weight was measured at the beginning and the end of the treatment period.

The PS-ω3 compound used in this study mimics the fatty acids composition of the mammalian brain PS, with respect to its DHA content (20%). Generally, in animal cells, the fatty acid composition of PS varies from tissue to tissue, but does not appear to resemble the precursor phospholipids, either because of selective utilization of specific molecular species for biosynthesis or because or re-modeling of the lipid via deacylation-reacylation reactions. In human plasma, 1-stearoyl-2-oleoyl and 1-stearoyl-2-arachidonoyl species predominate, but in brain and many others related tissues 1-stearoyl-2-docosahexaenoyl species are very abundant [O'Brien et al. (1964) $J$ $Lipid$ $Res.$ 5(3):329-38]. An early work by Yabuuchi et al. [Yabuuchi et al. (1968) $J$ $Lipid$ $Res.$ 9(1):65-7] established that the DHA content in bovine gray matter is up to 30% of the total fatty acids composition; most of the total amount of DHA was located at the sn-2 position (60%). It was the bovine brain PS that Toffano and Bruni reported in the early 1980's to be a pharmacologically active compound, which counteracts age-related changes in the central nervous system [Toffano et al. (1980) $Pharmacol.$ $Res.$ $Commun.$ 12:829-845].

Behavioral Testing

Water maze test, which was developed by Morris [Stewart, C A. and Morris, R G. (1993) The water maze. In: Behavioural Neuroscience: A Practical Approach. Vol. 1 (Saghal, A., ed.), pp. 107-122. Oxford University Press, New York, N.Y.], uses a circular tank (137 cm diameter, 35 cm deep) constructed of opaque white plastic. It is filled with water (21-22° C.) to a depth of 28 cm, and the water is rendered opaque by the addition of soluble, nontoxic white latex paint. In the place version of the maze, the rat develops a spatial map of the extra-maze cues, which it then uses to locate the platform. Thus the distance swum to the platform and the time taken in doing so should decrease over testing sessions (days) as the rat learns the location of the platform. Moreover, it is expected that if the rat has learned the location of the platform in relation to the extra-maze cues, its initial response on the probe trial will be to swim directly to the quadrant in which it expects to find the platform. Thus the distance swum (and time spent) in the target quadrant should be greater than that in the other two quadrants (excluding the start quadrant). The distance swum to the platform as well as the latency to reach the platform were monitored using the video-based tracking system. The behavioral testing was conducted during the dark cycle, when rats are normally most active.

The pool was located in a test room in which there were many extra-maze spatial cues. On the first three days, the rats were required to locate the hidden platform (15.5 cm×15.5 cm) situated 1 cm below the surface of the water. There were two acquisition testing sessions per day, with four trials per session. On each trial, the rat was placed, facing the wall, in one of the four quadrants in the tank, and allowed to swim for a maximum of 60 seconds. Once the rat found the platform, it remained there for 5 seconds before being returned to the holding cage, which was kept warm on a heating pad. If the rat failed to find the platform in that time, it was placed on it for 5 seconds before being returned to the holding cage. Each of the eight trials conducted each day was started from a different quadrant, with the order determined pseudorandomly (not twice from the same quadrant) and varying from day to day. The intertrial interval (ITI) was 120 seconds, counted from the end of one trial to the beginning of the next. On fourth day, followed by a session as abovementioned, the platform was removed from the tank, and a probe trial was conducted by placing the rat in the quadrant opposite to that of the platform and then allowing it to swim for 60 seconds. The day following the probe trial, the rats were tested with a session in which the maze was set up as previously described, followed by a session in which the platform was repositioned to the center of the opposite quadrant. The latency to find the platform on each trial was recorded. Scopolamine (1 mg/Kg) was intraperitoneally (i.p.) administered 30 minutes before the indicated trials.

Lipid Extraction and NMR Analyses

At the end of the behavioral testing, the rats were anesthetized with Halothane and then decapitated. Liver and brain tissues were quickly removed and stored (at −80° C.). The lipid fraction of the rat tissues were extracted using a modified version of the technique described by Bligh and Dyer 1959 [Bligh and Dyer, (1959) Can. J. Biochem. Physiol. 37, 911-917]. Briefly, 500-700 mg and 300-1200 mg of liver and brain tissues, respectively, were homogenized in a solution of CDCl3, methanol and CS-EDTA (1:2:2 v:v:v). The homogenates were further agitated using ultrasonic bath (10 min, 80° C.), followed by additional vigorous shaking (20 min). The relative ratio of the phospholipids in the homogenates was measured using high-resolution $^{31}$P-NMR at 121.MHZ using a 7.06 Tesla General Electric spectrometer.

These homogenates were further analyzed for their fatty acids distribution. First, the lipids extracts were desalted by reverse-phase chromatography using an RP-18 column [Williams et al. (1980) *J. Neurochem.;* 35, 266-269]; diheptadecanoyl phosphatidylcholine was added as internal standard before the loading on the column. Phospholipids were separated from neutral lipids, such as cholesterol, on silica gel plates (Merck 60) developed in isohexane: ether: formic acid 80:20:2 (v:v:v). The phospholipids spot was visualized by spraying primulin solution and compared with authentic phospholipids standards. Henicasonoic methyl ester (C21:0) was added as a 2nd internal standard and the phospholipids were converted to methyl esters by mild acid hydrolysis with 1% methanolic H2SO4 overnight at 50° C. The fatty acids profile of the different samples was determined by gas-liquid chromatography.

Results

Anti-dementia effects of bovine brain cortex-derived PS (BC-PS) has been demonstrated by several double-blind, placebo-controlled studies, see review by [Kidd P. (1996) *Alt Med. Rev.* 1(2):70-84]. In the past decade both BC-PS and soybean lecithin transphosphatidylated PS (SB-PS) were shown to recover the scopolamine-induced amnesia in rodent, although the fatty acids composition is considerably different between these compounds [Zanotti A et al. (1986) *Psychopharmacology* (Berl). 90(2):274-5.; Claro F. et al. (1999) Physiol Behav. 67(4):551-4; Sakai M. (1996) *Nutr Sci Vitaminol.* (Tokyo) 42(1):47-54; Furushiro M et al. (1997) *Jpn J. Pharmacol.* 75(4):447-50]. The means of PS administration in these studies was predominantly intravenous or intraperitoneal; although Furushiro et al. described also oral administration of SB-PS that antagonized amnesic effects of scopolamine. However, in the latter study the investigator used a considerable high dose of SB-PS, ranging between 60 to 240 mg/Kg.

In the presented study, rat diet was supplemented with the above-mentioned treatments (diets i, ii, iii, iv and v) for three months before the maze test was performed. In the acquisition stage (FIGS. 1A-1D) there is an expected and marked increase in the latency time to find the platform after the administration of scopolamine (1 mg/Kg) of all groups. Although the latency curves of MCT and PS-□3 groups are similar, there is a statistically smaller difference in the latency change, induced by scopolamine, in the PS-ω3 group with respect to the latency presented by the MCT group (P-value<0.07 Vs. P-value<0.0007, respectively). Similarly, the groups treated with SB-PS or LC-PUFA, demonstrated a reduced effect of scopolamine on their learning curves, with respect to the MCT group (see FIGS. 1A-1D). Having all groups learn the task at a similar rate, resembles data presented by Blokland et al. [Blokland et al. (1999) *Nutrition* 15(10): 778-83], which showed no difference between PS obtained from different sources and the empty vehicle, in a water maze test.

What is particular to the present trial is the accelerated rate in learning the task under the scopolamine sedation. This was not demonstrated previously [Furushiro et al. (1997) *id ibid.*; Suzuki et al., (2000) Jpn. J. Pharmacol. 84, 86-8]. Note that in these studies the rodent faced a different task (passive avoidance). In Suzuki et al. 2001 (J. Nutr. 131: 2951-6) the investigators utilized considerably older rats (24-25 months old) than the ones tested in the present trial. The latency time in the acquisition step was considerably longer for the aged rats compared to the young ones that were tested (eight weeks). Interestingly, although the latency time in the present trial of non-sedated rats is somewhat comparable to the younger rats tested by Suzuki et al. [Suzuki et al. (2001) *id ibid.*], the scopolamine-induced amnesia latency time in the MCT group resembles the one obtained at the described study for elderly rats. In conclusion, scopolamine induced a comparable long latency time in the control group (MCT). This effect was augmented to a different extent by long-term treatment of rats with either PS or LC-PUFA.

In the probe trial, the rats treated with PS-ω3 showed a distinctively higher tendency than MCT-treated ones (P<0.085) to be present at the zone in which the platform was located during the acquisition of the task (FIG. 2), indicating that the rats had learned the spatial location of the platform. Moreover, PS-ω3 treated rats presented a reduced tendency (P<0.08) to swim in the periphery zone, but rather spent in the central zone. These latter indications, presented by the PS-ω3 group are related to a higher adventurous characteristic and could be somewhat correlated with the open field behavior trial. Interestingly, in Blokland et al. [Blokland et al. (1999) *id ibid.*] BC-PS treated mice demonstrated a non-significant but clear tendency to be less adventurous in the open field behavior trial, by spending less time in the center area. With respect to the remarkable learning abilities demonstrated by the rats that were treated with PS-ω3, it is interesting to compare their performance in the Morris water maze task in the spatial probe test to the one obtained by the SB-PS treated animals by Suzuki et al [Suzuki et al (2001) *id ibid.*]. Though the percent of time spent in the quadrant where the platform was located is similar (~45%), it is remarkable that the dosage in the current study was merely one third of the administration levels in Suzuki et al 2001 (20 mg/kg vs. 60 mg/kg, respectively). Indeed, in the present study there was no significant change in the time that the SB-PS (20 mg/kg) treated rats spent in this quadrant when compared with the values obtained by the MCT-treated group [FIG. 1C and FIG. 1A, respectively]. In summary, the PS-ω3 treated group learning abilities were markedly higher than the control, in a considerably low level of PS administration. In addition, the rats treated with PS-ω3 were less conservative and more adventurous in studying the maze in the absence of the platform.

Finally, the most prominent and outstanding data obtained in the present study was the response to the repositioning of the platform. All groups presented a shorter latency in finding the platform at the first session, when compared to the one obtained by the MCT-treated group, under scopolamine sedation (FIGS. 3A-3D). These data suggest that LC-PUFA, and more potently PS, can attenuate scopolamine-induced amnesia, as previously presented by other studies (see selected references above).

Surprisingly, in the second session, there were no differences between the latency in finding the platform after its repositioning in all groups but the PS-ω3 treated group. In fact, it seemed that in all treatments but the PS-ω3 there was no learning process of the position of the platform. The PS-ω3 group presented a remarkably different behavior; it seemed that there was no lag in the learning of the repositioned platform in the rat treated with this anti-muscarinic drug. The ability of the PS-ω3 treated group to locate the platform after it had been repositioned seemed to be contradictory with the result obtained earlier in the spatial probe test (FIG. 2), where these rats showed preference for the third quadrant. Pearce and colleagues [Pearce et al. (1998) Nature 396: 75-77] attempted to resolve this discrepancy, by describing two means for memorizing a specific spatial location. One is to use a cognitive map that encodes information about the geometric relationship between the object and several land marks (the cognitive map method) and the other is the use of heading vectors that specify the direction and distance from a single landmark to the object (the heading vector method). In the present test, the rats could locate the platform from the above-mentioned cues and/or from the distance and direction with respect to the walls. In the acquisition and the spatial probe test, both methods contributed to the score of finding the platform. However, in the repositioning test, the cognitive abilities which are related to the heading vector method and the short-term memory (working memory), made the difference. The heading vector method, because the distance from the wall was not effected by the repositioning (just the quadrant), and the working memory due to the benefits in memorizing the areas already explored that enable an effective search in the pool.

It has been previously reported that the mechanism by which PS attenuates the scopolamine effect could be attributed not only to a beneficial effect on the cholinergic circuitry, but PS could also have an effect on the serotonergic neuronal system [Furushiro et al. (1997) id ibid.]. It appears that the presented data could be the result of more than one neuronal system alteration, possibly the dopaminergic. In an earlier study [Drago et al. (1981) Neurobiol Aging, 2(3):209-13], it was suggested that the alteration in the obtained behavioral changes between BC-PS treated aged rats to their control could be attributed not only to the modifications in cholinergic and serotonergic transmission, as described above, but also through affecting the catecholaminergic (like dopamine) system. In this study the facilitated acquisition of active avoidance behavior as studied in shuttle-box and pole jumping test situations, and the retention of active and passive avoidance responses were improved in the PS-treated rats. Tsakiris [Tsakiris, S. (1984) Z Naturforsch [C], 39(11-12):1196-8] reported on an indirect effect of PS on the dopamine related adenylyl cyclase, through membrane fluidity mechanism. Interestingly, it has also been reported [Chalon, et al. (1998) J. Nutr.; 128(12):2512-9] that enriched diet with high level of (n-3) PUFA could result in an effect on the cortical dopaminergic function. It is conceivable that the existence of LC-PUFA on the backbone of the phospholipids was highly beneficial in terms of such a multi-neurotransmitter mechanism.

The biochemical analyses of the present results in liver tissues (FIG. 4A) shows that in rats supplemented with PS for three months (SB-PS and PS-ω3) there was a notable increase in the levels of the primer phospholipids, i.e. phosphatidylcholine (PC). These data is consistent with early observations regarding the liver and its major role in the phospholipids uptake and the primary metabolism of most fatty acids. Wijendran and colleagues [Wijendran et al. (2002) Pediatr. Res. 51:265-272] described a study in which baboons were fed labeled LC-PUFA on the backbone of PC and triglycerides, and demonstrated that the levels of incorporation of LC-PUFA on a phospholipid backbone to the liver was higher than the extent of incorporation of LC-PUFA on the triglycerides backbone. In addition, PS levels of rats fed with PS-ω3 were elevated in cortex tissues analyses of phospholipids distribution (FIG. 4B), comparing with MCT. Interestingly, the phospholipids fatty acids profile of these cortices (Table 1) demonstrate a marked elevation in the DHA content of the rats fed with PS-ω3 ($P=0.007$). Similar elevation was noted for LC-PUFA fed rats, however to a reduced extent compared with PS-ω3 treatment (14.6 versus 17.5, respectively PS-ω3) and MCT (14.6 versus 12.3, respectively $P=0.02$). This difference in the DHA levels between the two omega-3 groups might suggest enhanced bioavailability of DHA when it is esterified to the backbone of phospholipids rather than to triglycerides. Similar conclusions were drawn by Lemaitre-Delaunay and colleagues [Lemaitre-Delaunay et al. (1999) J. Lipid Res.; 40:1867-1874], when they had study the kinetics and metabolic fate of labeled DHA on triglycerides versus its enrichment in lysophsphaytidylcholine, and by Wijendran et al. [Wijendran et al. (2002) id ibid.] in the above-mentioned baboons study.

Interestingly, this increase in DHA content in the cortices of both PS-ω3 and LC-PUFA fed rats is accompanied with a statistically significant decrease in the levels of oleic acids and to somewhat lower extent of linoleic acid (Table 1) in the phospholipids fraction. Similar changes in the ratios of the fatty acids profile was demonstrated by others, by feeding rodents with dietary fats enriched with LC-PUFA [for example: Yamamoto et al. (1987) J. Lipid Res. 28: 144-151]. The SB-PS group showed a very similar profile to the MCT group.

In sum, the improved performance in the Morris water maze test of the PS-ω3 treated rats under scopolamine sedation strongly supports the potency of PS-ω3 as an anti-dementia and age-associated memory impairment effects. This cognitive enhancement is further supported by the biochemical evidence of the elevated phospholipids levels in the liver and brain tissues (FIGS. 4A-4B), and with elevated levels of DHA attached to the phospholipids from the cortex of the PS-ω3 fed rats.

Table 1 summarizes the effect of dietary LC-PUFA from different sources on the fatty acids profile in cerebral phospholipids from elderly Wistar rats. Fatty acids from the purified phospholipids fraction were analyzed by gas-liquid chromatography. The major fatty acids are expressed as % of total fatty acids in the phospholipids. Values represent mean±S.D. of four different rats per treatment. Statistical significant between different supplements and MCT group is presented as followed: *$P<0.05$; **$P<0.01$.

TABLE 1

| Fatty acids | MCT | LC-PUFA | SB-PS | PS-ω3 |
|---|---|---|---|---|
| C16:0 | 12.9 ± 1.4 | 14.6 ± 4.7 | 13.7 ± 4.7 | 13.6 ± 4.4 |
| C16:1 | 1.0 ± 0.7 | 1.0 ± 0.3 | 1.5 ± 0.4 | 1.5 ± 0.8 |
| C18:0 | 17.9 ± 1.0 | 20.1 ± 1.3* | 17.2 ± 2.8 | 18.0 ± 5.5 |
| C18:1 (n-9) | 36.5 ± 1.8 | 32.0 ± 2.8* | 37.0 ± 6.8 | 30.7 ± 4.1* |
| C18:1 (n-7) | 3.7 ± 0.5 | 4.3 ± 0.2* | 4.0 ± 0.3 | 4.8 ± 1.5 |
| C18:2 | 7.2 ± 0.7 | 4.5 ± 0.6** | 7.1 ± 2.6 | 5.1 ± 2.7 |

TABLE 1-continued

| Fatty acids | MCT | LC-PUFA | SB-PS | PS-ω3 |
|---|---|---|---|---|
| C20:1 | 2.5 ± 0.5 | 2.9 ± 0.8 | 2.1 ± 0.4 | 2.3 ± 0.3 |
| C22:6 | 12.3 ± 1.7 | 14.6 ± 0.6* | 12.4 ± 3.2 | 17.5 ± 2.4** |
| C24:1 | 3.4 ± 1.0 | 3.3 ± 1.3 | 2.8 ± 0.9 | 2.0 ± 1.2* |
| rest | 2.7 ± 0.1 | 2.8 ± 0.4 | 2.1 ± 0.9 | 4.5 ± 3.0 |

Example 2

PS-omega-3 in the Treatment of ADHD Children

Attention-deficit/hyperactivity disorder (ADHD) encompasses a broad constellation of behavioural and learning problems and its definition and diagnosis remain controversial [Kamper (2001) *J. Pediatr.* 139:173-4; Richardson et al. (2000) *Prostaglandins Leukot. Essent. Fatty Acids,* 63(1-2): 79-87]. The etiology of ADHD is acknowledged to be both complex and multi-factorial. Traditionally, ADHD is the diagnosis used to describe children who are inattentive, impulsive, and/or hyperactive. Roughly 20-25% of children with ADHD show one or more specific learning disabilities in math, reading, or spelling [Barkley, R. A. (1990) *Attention-deficit hyperactivity disorder: a handbook for diagnosis and treatment.* New York: Guilford Press]. Children with ADHD often have trouble performing academically and paying attention, and may be disorganized, have poor self-discipline, and have low self-esteem. A conservative estimate is that 3-5% of the school-age population has ADHD [American Psychiatric Association. Diagnostic and statistical manual of mental disorders. 4th ed. (DSM-IV) Washington, D.C.: American Psychiatric Association, 1994]. Treatments for ADHD include behavior therapy and medications, mainly methylphenidate (Ritalin™). Psychostimulant drugs and antidepressants are often used to calm children with ADHD, with an effectiveness rate of ~75% (Swanson et al. Except Child 1993; 60:154-61). The advantages of using these medications include rapid response, ease of use, effectiveness, and relative safety. Disadvantages include possible side effects, including decreased appetite and growth, insomnia, increased irritability, and rebound hyperactivity when the drug wears off [Ahmann et al. (1993) *Pediatrics;* 91:1101-6]. Moreover, these medications do not address the underlying causes of ADHD. Thus, studies to elucidate the potential contributors to the behavior problems in ADHD may lead to more effective treatment strategies for some children.

Omega-3 fatty acids are specifically implicated in maintaining central nervous system function. Deficiency of n-3 fatty acids in rats and monkeys has been associated with behavioral, sensory, and neurological dysfunction [Yehuda et al. (1993) *Proc. Natl. Acad. Sci. USA;* 90:10345-9; Reisbick et al. (1994) *Physiol. Behav.* 55:231-9; Enslen et al. (1991) *Lipids;* 26:203-8]. Several studies have focused on essential fatty acid metabolism in children with ADHD [Colquhoun et al. (1981) *Med Hypotheses;* 7:673-679]. Children with hyperactivity have been reported to be more thirsty than normal children and have symptoms of eczema, asthma, and other allergies [Mitchell et al. (1987) *Clin. Pediatr.;* 26:406-11]. For example, in a cross-sectional study in 6-12-y-old boys recruited from central Indiana, it was showed that 53 subjects with ADHD had significantly lower proportions of key fatty acids in the plasma polar lipids [arachidonic acid (AA; 20:4n-6), eicosapentaenoic acid (EPA; 20:5n-3), and docosahexaenoic acid (DHA; 22:6n-3)] and in red blood cell total lipids (20:4n-6 and 22:6n-6) than did 43 control subjects [Stevens et al. (1995) *Am. J. Clin. Nutr.;* 62:761-8]. However, recent publications [Hirayama et al. (2004) *Eur. J. Clin. Nutr.;* 58(3):467-73; Voigt et al. (2001) *J. Pediatr.;* 139(2):189-96] that investigated whether DHA supplementation would result with ameliorate the symptoms in ADHD children, suggested that careful attention should be paid as to which fatty acid(s) is used. In these studies DHA supplementation had demonstrated only marginal if any beneficial effects.

Recently, it has been suggested that one of the possible solutions to the nutrient deficiencies which are common in ADHD, could be PS supplementation [Kidd (2000) *Altern Med. Rev.;* 5(5):402-28].

Method

Subjects and Diet

Ninety 8-to-13-year old children diagnosed according to the DSM-IV as ADHD, were assigned randomly, in a double-blind fashion to receive PS-ω3 (300 mg/d; containing total 450 mg/d DHA/EPA), 450 mg/d DHA/EPA or canola oil (30 per group) for two months, while not taking stimulant medication or other supplements. Characterizing the subject as ADHD included a score lower than −1.8 in the Test of Variables of Attention.

Data Analysis

At the conclusion of the trial, ADHD children were scored according to parental behavioural rating scales (Connors' Rating scale).

Results and Discussion

Use of complementary therapies is particularly common among patients with chronic, incurable, or frequently relapsing conditions. For example, use of complementary and alternative medical therapies (CAM) is common in children with cancer, asthma, and cystic fibrosis. Parents or subjects who seek CAM typically do so because such therapies are more consistent with their values, are more empowering, and are perceived as more natural and less risky than conventional treatments. The majority of these patients do not abandon mainstream therapies but use herbs and other forms of CAM as adjunctive treatments. Only a minority (<40%) talk with their pediatricians about their use of CAM. Because of the stigma and side effects that accompany use of stimulant medications, many families turn to CAM to treat ADHD. Typically, only 70% of children respond to stimulants such as Ritalin™ and of those who do, approximately half report side effects from their medications. In an Australian survey of 290 families seen at a multidisciplinary referral center for ADHD, 64% had tried at least one "other therapy," most commonly dietary restriction, multivitamin supplementation, and occupational therapy [Stubberfield et al. (1999) *J Paediatr Child Health;* 35:450-3].

In the presented study the different supplementation was formulated into a popular chocolate paste (see below). Using this matrix enable the parents to administer the treatments in a non-conventional form to their children and provided a reduced organoleptic effect characteristic of the marine-derived compounds (see below).

The parental rating survey, at the end of the treatment period, measured the attention deficit, hyperactivity and impulsivity of the children, as well as the aggression as assessed by parents, teachers, siblings and peers. The results indicate a distinctively large placebo effect. This effect is somewhat reduced if the placebo-treated ADHD children that failed to complete the study due to severe behavioral deterioration are taken into consideration. It seemed that most of these children insisted on reassigning for Ritalin™ administration. However, the present data also clearly demonstrate PS-ω3 as a potent agent. All in all, ~70% of the parents of the PS-ω3 treated ADHD children indicated some improvement in the behavioural score of their children, whereas 50% of these parents provided clear indications for multiple beneficial effect of the supplement on their children behavior. This prominent effect is 2.2-fold higher than the improvement obtained by placebo (~30%). Comparison of the parental scoring of LC-PUFA on ADHD children behavior with the parallel rating that followed three months of PS-ω3 administration, point at the latter to have a higher score. While both compounds demonstrated similar extent of marginal improvement, PS-ω3 had a marked higher rate of substantial improvement (47% versus 35%, respectively) with the lowest rats of lack or deteriorating effects (21% & 11% versus 26% and 17%, respectively). These effects of PS-ω3 supplementation could be attributed to both enhanced bioavailability of omega-3 fatty acids and through PS well documented effects on mood, stress and anxiety.

Example 3

Effect of PC-DHA Consumption in ApoE° Mice

Methods
Animal Diet

Apolipoprotein E deficient (ApoE°) mice [Hayek T. et al. (1994) *Biochem. Biophys. Res. Commun.* 201:1567-1574] at 8 weeks of age, were assigned randomly (5 mice each) to LC-PUFA enriched lecithin (30% omega-3 of total fatty acids composition; PC-DHA group) or placebo. The mice were fed, besides the regular chow diet, once every three days with either 25 μl PC-DHA or PBS, via oral gavage, during 10 weeks.

Each mouse consumed approximately 5 mL of water/day, and 5 g of chow/day.
Serum Lipids Peroxidation Serum was diluted 1:4 in PBS. Serum susceptibility to oxidation was determined by incubating serum sample with 100 mM of the free radical generating compound, 2'-2'-azobis 2'-amidinopropane hydrochloride (AAPH), which is an aqueous soluble azo compound that thermally decomposes to produce peroxyl radicals at a constant rate. The formation of thiobarbituric reactive substances (TBARS) and of lipid peroxides was measured and compared to serum that was incubated under similar conditions, but without AAPH.
Results and Discussion:

ApoE° mice are widely used as an animal model for atherosclerosis as they develop severe hypercholesterolemia and atherosclerotic lesions on a chow diet. Moreover, accelerated atherosclerosis is associated with increased lipid peroxidation of plasma lipoproteins and arterial cells in these mice [Hayek T. et al. (1994) id ibid.; Keidar S. (1998) *Life Sci.* 63:1-11].

FIG. 6 shows how prolonged PC-DHA consumption by ApoE° mice resulted in a clear tendency (P<0.10) to reduce the serum susceptibility to AAPH-induced oxidation by 16% (in comparison to placebo).
Organoleptic Issues The utilization of omega-3 lipids in a variety of applications, and especially as ingredient of functional foods, is hindered due to their distinct fish odor. Thus, another advantage of the omega-3 enriched phospholipids ingredients of the invention is that they have reduced odor or taste of omega-3 acyl moieties, due to the covalent binding of these groups to the PS backbone. This increases the vapor pressure of these materials, hence reducing their distinct aroma. Thus, the covalent binding of the omega-3 fatty acids to the phospholipid backbone, especially PS, alters and improves their taste properties. Moreover, the PS ingredient of the invention also offers enhanced stability to the oxidation sensitive omega-3 fatty acids. Phospholipids in general, and PS in particular, are known to act as anti-oxidants and stabilizers.

These benefits make this novel phospholipids' preparation of the invention highly beneficial and important in a variety of applications and especially in functional foods, where stability, aroma and taste are fundamental requirements.

Furthermore, these novel ingredients can be formulated with additional lipids for an even enhanced bio-functionality and efficacy.

The starting compound used for the above-mentioned clinical trial in ADHD patients, was LC-PUFA enriched PS mixed with fish oil. Originally, this product and the control fish oil were formulated in food products like energy bars; however the responses from expert panels were categorically devastating, pointing at severe organoleptic problems. In order to overcome this taste barrier the PS-ω3 product of the invention was de-oiled. The end-product of this process was a paste that when reformulated with either inert or dominant-organoleptic saturated fats could be easily formulated in chocolate bars, chocolate spread, chocolate coated cornflakes, low-fat dairy products or concentrated milk. Each one of these formulations had an evidently reduced organoleptic objection from both the expert panels and the trial volunteers.

The polar lipids derivatives of PUFA, such as the PS-PUFA derivatives have exhibited high stability as a preparation and additionally in several food applications, used in the clinical trials of this invention. This stability, of these sensitive compounds is emerging from the covalent combination of phospholipids, known in the past to be used as preservatives and of the un-stable PUFA moieties.

The stability of a commercially prepared fish oil (omega-3 fatty acid) for laboratory rodent diet [Lytle et al. (1992) *Nutr Cancer,* 17(2):187-94] or as an enrichment in spreadable fats [Kolanowski et al. (2001) *Int J Food Sci Nutr.;* 52(6):469-76] was addressed by several studies as the public awareness towards the beneficial effects of LC-PUFA increased. A major effort was directed at maintaining the oxidative stability of the fish oil, as these fatty acids are subject to rapid and/or extensive oxidation and other chemical changes by exposure to air, light, or heat during processing or when stored for various lengths of time. The common solution presented in these studies was supplementation the fish oil matrix with antioxidants like butylated hydroxytoluene, butylated hydroxyquinone and alpha-tocopherol, or alternatively, dilution of concentrated fish oil to a limit of 1% in a saturated fats matrix. However, Song and colleagues [Song et al. (1997) *Biosci Biotechnol Biochem.;* 61(12):2085-8] had already evaluated the peroxidative stability of DHA-containing oils the form of phospholipids, triglycerides, and ethyl esters in the dark at 25° C. in a bulk phase during 10 weeks storage. They had shown that DHA-containing oil in the form of phospholipids was more resistant to the oxidative degradation of DHA than that in the form of triglycerides and ethyl esters in a bulk phase.

The abovementioned PS-ω3 containing products utilized for the clinical studies were tested for their shelf-life and stability in room temperature. The enriched PS-ω3 formulated in condensed milk (1 g product per 10 ml milk) was analyzed by $^{31}$P-NMR for stability in cycles of freeze-thawing for a week, and was found to be stable. In the second phase, PS-ω3 in a chocolate paste matrix (0.75 g product per 20 g chocolate spread) was tested for stability after two weeks storage in room temperature. This formulation also presented a stable percentage of PS, in $^{31}$P-NMR analysis. In conclusion, we had been able to establish that ω-3 containing phospholipids are highly stable in room temperature, as well as in freezing-thawing cycles, as oppose to ω-3 containing triglycerides known to rapidly decay after antioxidant consumption.

what is claimed is:

1. A method of treating a subject suffering from a cognitive or mental condition or disorder which comprises administering to the subject a therapeutically effective amount of a preparation, comprising serine glycerophospholipids which comprise a non-mammalian derived mixture of serine glycerophospholipids comprising EPA and serine glycerophospholipids comprising DHA, wherein each such serine glycerophospholipid comprising EPA and each such serine glycerophospholipid comprising DHA has the formula (I):

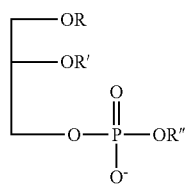

wherein R" is serine;
wherein one of R or R' is acyl EPA or acyl DHA and the other of R or R' is hydrogen or an acyl group;
wherein the combined amount of EPA and DHA present in such mixture of serine glycerophospholipids constitutes 10-50% by weight of the total fatty acids content of the serine glycerophospholipids in said preparation;
wherein the condition or disorder is selected from the group consisting of a learning disorder, an age-associated memory impairment, a cognitive decline, and attention deficit hyperactivity disorder (ADHD); and wherein the mixture enhances the bioavailability of DHA.

2. The method according to claim 1, wherein said glycerophospholipid conjugate is prepared by enzymatic transphosphatidylation of a lipid source selected from the group consisting of plant, animal or microorganism sources.

3. The method according to claim 1 wherein the preparation is present in a pharmaceutical composition.

4. The method according to claim 3, wherein the pharmaceutical composition further comprises at least one pharmaceutically acceptable additive, diluent or excipient.

5. The method according to claim 4, wherein the pharmaceutical composition further comprises at least one additional pharmaceutically active agent.

6. The method according to claim 3, wherein the pharmaceutical composition is delivered orally or intravenously.

7. The method according to claim 1 wherein the preparation is present in a nutraceutical composition.

8. The method according to claim 7, wherein said nutraceutical composition is in the form of a softgel capsule, tablet, syrup, or other dietary supplement delivery system.

9. The method according to claim 1 wherein the preparation is present in a functional food.

10. The method according to claim 9, wherein the functional food is a dairy product, ice-cream, biscuit, soy product, bakery, pastry, bread, sauce, soup, prepared food, frozen food, condiment, confectionary, oil, fat, margarine, spread, filling, cereal, instant product, drink, shake, infant formula, infant food, bar, snack, candy or chocolate product.

* * * * *